(12) United States Patent  
Yamatani

(10) Patent No.: US 12,398,148 B2  
(45) Date of Patent: Aug. 26, 2025

(54) POLYCYCLIC COMPOUND AND ORGANIC ELECTROLUMINESCENCE DEVICE INCLUDING THE SAME

(71) Applicant: SAMSUNG DISPLAY CO., LTD., Yongin-si (KR)

(72) Inventor: Akinori Yamatani, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 615 days.

(21) Appl. No.: 15/666,682

(22) Filed: Aug. 2, 2017

(65) Prior Publication Data

US 2018/0123057 A1     May 3, 2018

(30) Foreign Application Priority Data

Nov. 1, 2016    (KR) .................. 10-2016-0144690  
Jan. 10, 2017    (KR) .................. 10-2017-0003666

(51) Int. Cl.

| | | |
|---|---|---|
| C07D 491/153 | (2006.01) | |
| C07D 209/80 | (2006.01) | |
| C07D 471/14 | (2006.01) | |
| C07D 487/04 | (2006.01) | |
| C07D 491/052 | (2006.01) | |
| C07D 491/147 | (2006.01) | |
| C07D 491/22 | (2006.01) | |
| C07D 493/14 | (2006.01) | |
| C07D 495/14 | (2006.01) | |
| C07F 7/08 | (2006.01) | |
| H10K 50/11 | (2023.01) | |
| H10K 50/15 | (2023.01) | |
| H10K 50/16 | (2023.01) | |
| H10K 50/17 | (2023.01) | |

(Continued)

(52) U.S. Cl.  
CPC ....... C07D 491/153 (2013.01); C07D 209/80 (2013.01); C07D 471/14 (2013.01); C07D 487/04 (2013.01); C07D 491/052 (2013.01); C07D 491/147 (2013.01); C07D 491/22 (2013.01); C07D 493/14 (2013.01); C07D 495/14 (2013.01); C07F 7/0816 (2013.01); H10K 85/40 (2023.02); H10K 85/653 (2023.02); H10K 85/654 (2023.02); H10K 85/655 (2023.02); H10K 85/657 (2023.02); H10K 85/6572 (2023.02); H10K 85/6574 (2023.02); H10K 50/11 (2023.02); H10K 50/156 (2023.02); H10K 50/16 (2023.02); H10K 50/17 (2023.02); H10K 50/81 (2023.02); H10K 50/82 (2023.02); H10K 2101/10 (2023.02)

(58) Field of Classification Search  
CPC ............ C07D 491/04; C07D 491/048; C07D 491/052; C07D 491/056; C07D 491/06; C07D 491/14; C07D 491/147; C07D 491/153; C07D 491/16; C07D 491/22; C07D 493/04; C07D 493/14; C07D 493/16; C07D 493/22; C07D 495/04; C07D 495/14; C07D 495/16; C07D 495/22; C07D 497/04; C07D 497/14; C07D 497/16; C07D 497/22; C07D 498/04; C07D 498/14; C07D 498/16; C07D 498/22; C07D 513/04; C07D 513/14; C07D 513/16; C07D 513/22; C07D 209/80; C07D 471/04; C07D 471/16; C07D 471/22; C07D 487/04; C07D 487/16; C07D 487/22; H01L 51/0061; H01L 51/0071; H01L 51/0072; H01L 51/0073; H01L 51/0074; H01L 51/0065; H01L 51/0067; H01L 51/0068; H10K 85/40; H10K 85/654; H10K 85/655; H10K 85/6574; H10K 85/657; H10K 85/653; H10K 85/6572; C07F 7/0816

See application file for complete search history.

(56) References Cited

U.S. PATENT DOCUMENTS

| | | | |
|---|---|---|---|
| 10,700,296 B2 | 6/2020 | Yamatani | |
| 2003/0028024 A1* | 2/2003 | Rauchschwalbe ... | C08G 61/126 |
| | | | 544/345 |

(Continued)

FOREIGN PATENT DOCUMENTS

| | | | |
|---|---|---|---|
| JP | 2005022268 A | * | 1/2005 |
| JP | 2005-255575 A | | 9/2005 |

(Continued)

OTHER PUBLICATIONS

Screenshot of Merriam Webster's definition of "adjacent", 2019, p. 1. (Year: 2019).*

(Continued)

*Primary Examiner* — Dylan C Kershner  
(74) *Attorney, Agent, or Firm* — Womble Bond Dickinson (US) LLP

(57) ABSTRACT

Disclosed are a polycyclic compound and an organic electroluminescence device including the same. The polycyclic compound according to an embodiment is represented by the following Formula 1, wherein in Formula 1, Cy1 to Cy3, $L_1$ to L4, and m are as respectively defined in the detailed description of the current disclosure.

[Formula 1]

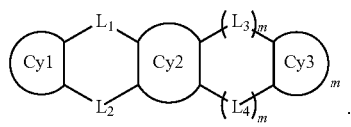

21 Claims, 2 Drawing Sheets

(51) Int. Cl.
  *H10K 50/81*   (2023.01)
  *H10K 50/82*   (2023.01)
  *H10K 85/40*   (2023.01)
  *H10K 85/60*   (2023.01)
  *H10K 101/10*  (2023.01)

(56) References Cited

U.S. PATENT DOCUMENTS

| | | | | |
|---|---|---|---|---|
| 2003/0209708 | A1* | 11/2003 | Kubota | H10K 50/8445 |
| | | | | 257/40 |
| 2006/0110623 | A1 | 5/2006 | Funahashi et al. | |
| 2008/0231178 | A1* | 9/2008 | Park | H10K 50/17 |
| | | | | 313/504 |
| 2009/0212688 | A1* | 8/2009 | Song | H01L 51/508 |
| | | | | 313/504 |
| 2011/0266533 | A1* | 11/2011 | Buesing | C07D 219/02 |
| | | | | 257/40 |
| 2014/0042370 | A1* | 2/2014 | Martynova | H01L 51/0071 |
| | | | | 546/37 |
| 2019/0019957 | A1* | 1/2019 | Hildebrandt | H01L 51/0068 |

FOREIGN PATENT DOCUMENTS

| | | | |
|---|---|---|---|
| JP | 2005255573 A | * | 9/2005 |
| KR | 10-2007-0084110 A | | 8/2007 |
| KR | 20110111093 A | * | 10/2011 |
| KR | 10-2011-0124243 A | | 11/2011 |
| KR | 10-1321988 B1 | | 10/2013 |
| KR | 10-2013-0120648 A | | 11/2013 |
| KR | 10-2016-0079548 A | | 7/2016 |
| KR | 20170002186 A | * | 1/2017 |
| KR | 10-2018-0051748 A | | 5/2018 |
| WO | WO 2007/110228 A1 | | 10/2007 |
| WO | WO 2012/143080 A2 | | 10/2012 |
| WO | WO 2015/167223 A1 | | 11/2015 |

OTHER PUBLICATIONS

Choi Tae Jin et al., Machine Translation of KR-20170002186-A (2017) pp. 1-46. (Year: 2017).*

Ashby et al., "The Direct Bradsher Reaction. Part 11.I Synthesis of Pyrylium and Thiopyrylium Salts", J. Chem. Soc., Perkin Trans. 1 (1973) pp. 1104-1107. (Year: 1973).*

Grol et al., "Synthesis of Isomeric Thienobenzothiazines and Their Effect on Dopamine Metabolism in Rat Brain" Journal of Medicinal Chemistry. 1980, vol. 23, pp. 322-324. (Year: 1980).*

Choi et al., machine translation of KR-20170002186-A (2017) pp. 1-26. (Year: 2017).*

Bozzo et al. ("A Short Synthesis for the Preparation of Polycyclic Systems Containing Pyridine Ring by Diels-Alder Reaction" Journal of Heterocyclic Communications, vol. 2, No. 2 (1996) pp. 163-167. (Year: 1996).*

Omura H, machine translation of JP-2005022268-A (2005) pp. 1-15. (Year: 2005).*

Cava et al., "A Photochemical Route to the Thieno[c]cyclobutene System" J. Org. Chem., vol. 39, No. 2 (1974) pp. 206-209. (Year: 1974).*

Garratt et al., "Base Catalyzed Rearrangement of Bispropargyl Sulfides, Ethers, and Amines. The Synthesis of Novel Heterocyclic Systems." Journal of the American Chemical Society, vol. 97, No. 11 (1975) pp. 3255-3257. (Year: 1975).*

Varlamov et al., Reactions of 4,4,9-trimethyl-4,9-dihydro-4-silanaphtho[3,2-b]thiophen-9-one with nucleophilic and electrophilic reagents. Chemistry of Heterocyclic Compounds, vol. 34, No. 5 (1998) pp. 545-549. (Year: 1998).*

Yin et al., "Preparation of Allenephosphoramide and Its Utility in the Preparation of 4,9-Dihydro2H-benzo[f]isoindoles." Organic Letters, vol. 13, No. 5 (2011) pp. 940-943. (Year: 2011).*

Lee et al., "Synthesis and Properties of Novel Dithienothiasiline Derivatives" Organometallics, vol. 23 (2004) pp. 5365-5371. (Year: 2004).*

Je J et al., machine translation of KR-20110111093-A (2011) pp. 1-21. (Year: 2011).*

Kunai A et al., machine translation of JP-2005255573-A (2005) pp. 1-20. (Year: 2005).*

Tagawa et al., "Synthesis of hexagonal shape-persistent cyclophane with D2h symmetry" Tetrahedron Letters, vol. 57 (2016) pp. 4079-4081. (Year: 2016).*

Furukawa, et al., Development of a Sila-Friedel-Crafts Reaction and Its Application to the Synthesis of Dibenzosilole Derivatives. J. Am. Chem. Soc., 2009, 131, 14192.

* cited by examiner

POLYCYCLIC COMPOUND AND ORGANIC ELECTROLUMINESCENCE DEVICE INCLUDING THE SAME

CROSS-REFERENCE TO RELATED APPLICATIONS

Korean Patent Application Nos. 10-2016-0144690, filed on Nov. 1, 2016, and 10-2017-0003666, filed on Jan. 10, 2017, in the Korean Intellectual Property Office, and entitled: "Polycyclic Compound and Organic Electroluminescence Device Including the Same," are each incorporated by reference herein in its entirety.

BACKGROUND

1. Field

Embodiments relate to a polycyclic compound and an organic electroluminescence device including the same.

2. Description of the Related Art

The development of an organic electroluminescence display device as an image display device is being actively conducted. The organic electroluminescence display device may be implemented as a self-luminescence display device in which holes and electrons injected from a first electrode and a second electrode recombine in an emission layer, and a luminescent material including an organic compound in the emission layer emits light to attain display.

An organic electroluminescence device may include, for example, a first electrode, a hole transport layer disposed on the first electrode, an emission layer disposed on the hole transport layer, an electron transport layer disposed on the emission layer, and a second electrode disposed on the electron transport layer. Holes are injected from the first electrode, and the injected holes move via the hole transport layer and are injected to the emission layer. Meanwhile, electrons are injected from the second electrode, and the injected electrons move via the electron injection layer and are injected to the emission layer. The holes and electrons injected to the emission layer recombine to generate excitons in the emission layer. The organic electroluminescence device emits light using light generated during the transition of the excitons from an excited state to a ground stage. In addition, the organic electroluminescence device is not limited to the above-described configuration, but various modifications thereof may be possible.

SUMMARY

Embodiments are directed to a polycyclic compound represented by the following Formula 1.

[Formula 1]

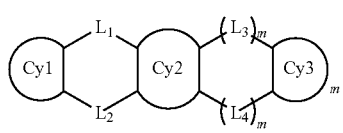

where $L_1$ to $L_4$ are each independently a substituted or unsubstituted divalent alkyl group having 1 to 10 carbon atoms, a substituted or unsubstituted divalent amino group, a substituted or unsubstituted divalent oxy group, a substituted or unsubstituted divalent thio group, a substituted or unsubstituted divalent sulfoxy group, a substituted or unsubstituted divalent phosphine oxide group, or a substituted or unsubstituted divalent silyl group, m is 0 or 1, and Cy1 to Cy3 are each independently represented by the following Formula 2-1 or 2-2, where one of Cy1 or Cy2 is represented by the following Formula 2-2:

[Formula 2-1]

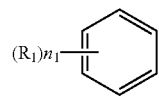

[Formula 2-2]

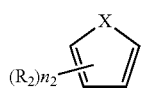

where X is one of O, S, or $NY_1$, $R_1$ and $R_2$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted oxy group, a substituted or unsubstituted thio group, a substituted or unsubstituted boron group, a substituted or unsubstituted sulfoxy group, a substituted or unsubstituted phosphine oxide group, a substituted or unsubstituted carbonyl group, a substituted or unsubstituted amino group, or a substituted or unsubstituted silyl group, $Y_1$ is a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted boron group, a substituted or unsubstituted sulfoxy group, a substituted or unsubstituted phosphine oxide group, a substituted or unsubstituted carbonyl group, or a substituted or unsubstituted silyl group, $n_1$ is an integer of 0 to 4, and $n_2$ is an integer of 0 to 2.

In an embodiment, the polycyclic compound represented by Formula 1 may be represented by one of the following Formulae 3-1 to 3-4.

[Formula 3-1]

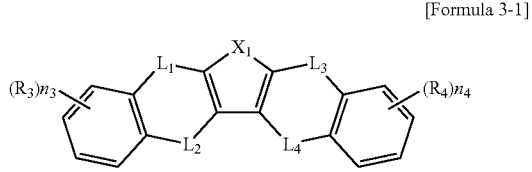

[Formula 3-2]

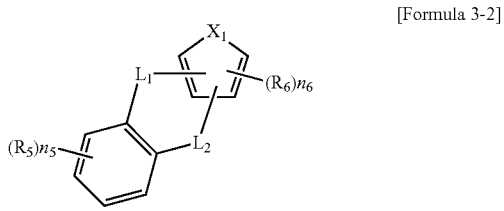

[Formula 3-3]

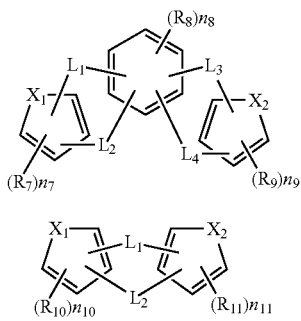

[Formula 3-4]

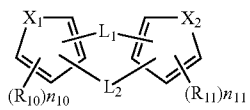

where $X_1$ and $X_2$ are each independently one of O, S, or $NY_1$. $R_3$ to $R_{11}$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted oxy group, a substituted or unsubstituted thio group, a substituted or unsubstituted boron group, a substituted or unsubstituted sulfoxy group, a substituted or unsubstituted phosphine oxide group, a substituted or unsubstituted carbonyl group, a substituted or unsubstituted amino group, or a substituted or unsubstituted silyl group, $n_3$ to $n_5$ are each independently an integer of 0 to 4, $n_6$ to $n_{11}$ are each independently an integer of 0 to 2, and $Y_1$ and $L_1$ to $L_4$ are the same as defined above.

In an embodiment, the polycyclic compound represented by Formula 3-2 may be represented by one of the following Formula 3-2-1 or 3-2-2.

[Formula 3-2-1]

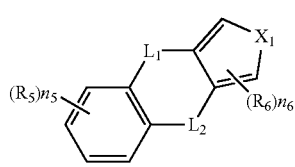

[Formula 3-2-2]

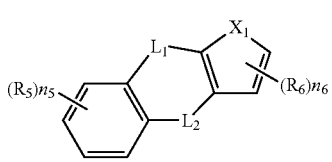

where $L_1$, $L_2$, $R_5$, $R_6$, $X_1$, $n_5$ and $n_6$ are the same as defined above.

In an embodiment, the polycyclic compound represented by Formula 3-3 may be represented by the following Formula 3-3-1 or 3-3-2.

[Formula 3-3-1]

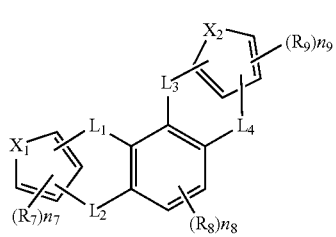

[Formula 3-3-2]

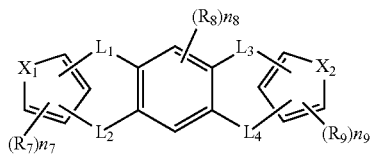

where $L_1$, $L_2$, $L_3$, $L_4$, $R_7$, $R_8$, $R_9$, $X_1$, $X_2$, $n_7$, $n_8$ and $n_9$ are the same as defined above.

In an embodiment, the polycyclic compound represented by Formula 3-4 may be represented by the following Formula 3-4-1 or 3-4-2.

[Formula 3-4-1]

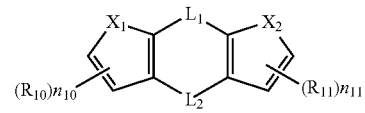

[Formula 3-4-2]

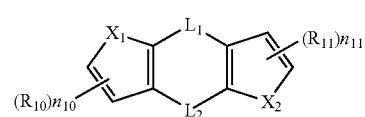

where $L_1$, $L_2$, $R_{10}$, $R_{11}$, $X_1$, $X_2$, $n_{10}$ and $n_{11}$ are the same as defined above.

In an embodiment, $L_1$ to $L_4$ may each independently be a substituted or unsubstituted divalent alkyl group having 1 to 10 carbon atoms, a substituted or unsubstituted divalent silyl group, a substituted or unsubstituted divalent oxy group, or a substituted or unsubstituted divalent thio group.

In an embodiment, $L_1$ to $L_4$ may each independently be a divalent alkyl group having 1 to 10 carbon atoms and substituted with a substituted or unsubstituted aryl group having 6 to 15 carbon atoms for forming a ring, an amino group substituted with a substituted or unsubstituted aryl group having 6 to 15 carbon atoms for forming a ring, or a silyl group substituted with a substituted or unsubstituted aryl group having 6 to 15 carbon atoms for forming a ring.

In an embodiment, $R_1$ and $R_2$ may each independently be a substituted or unsubstituted aryl group having 6 to 15 carbon atoms for forming a ring, or the substituted or unsubstituted silyl group.

In an embodiment, an organic electroluminescence device includes a first electrode, a hole transport region provided on the first electrode, an emission layer provided on the hole transport region, an electron transport region provided on the emission layer, and a second electrode provided on the electron transport region, wherein the hole transport region includes a polycyclic compound according to an embodiment.

In an embodiment, the hole transport region may include a hole injection layer disposed on the first electrode, and a hole transport layer disposed on the hole injection layer, wherein the hole transport layer includes a polycyclic compound according to an embodiment.

In an embodiment, the hole transport region may include a hole injection layer disposed on the first electrode, a first hole transport layer disposed on the hole injection layer, and a second hole transport layer disposed on the first hole transport layer and adjacent to the emission layer, wherein the second hole transport layer includes the polycyclic compound represented by Formula 1.

BRIEF DESCRIPTION OF THE FIGURES

Features will become apparent to those of ordinary skill in the art by describing in detail exemplary embodiments with reference to the attached drawings in which.

DETAILED DESCRIPTION

Figure 1:
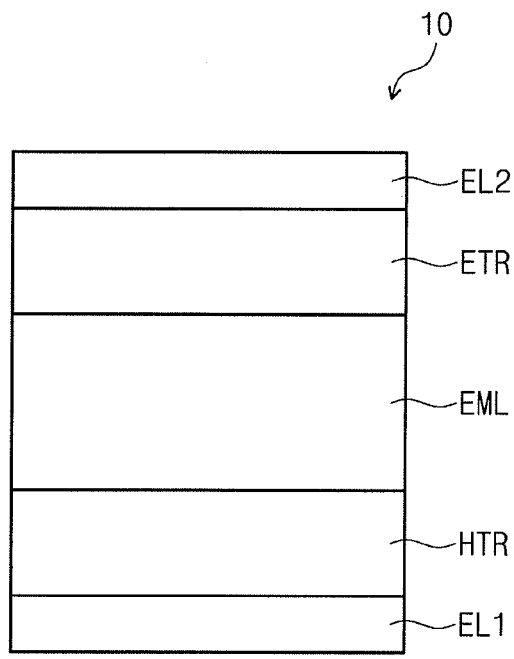
FIG. 1 illustrates a cross-sectional view schematically illustrating an organic electroluminescence device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art. In the drawing figures, the dimensions of layers and regions may be exaggerated for clarity of illustration. Like reference numerals refer to like elements throughout.

It will be understood that, although the terms first, second, etc. may be used herein to describe various elements, these elements should not be limited by these terms. These terms are only used to distinguish one element from another element. Thus, a first element could be termed a second element without departing from the teachings of the present invention. Similarly, a second element could be termed a first element. As used herein, the singular forms are intended to include the plural forms as well, unless the context clearly indicates otherwise.

It will be further understood that the terms "comprises" and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof. It will also be understood that when a layer, a film, a region, a plate, etc. is referred to as being 'on' another part, it can be directly on the other part, or intervening layers may also be present. On the contrary, it will be understood that when a layer, a film, a region, a plate, etc. is referred to as being 'under' another part, it can be directly under, and one or more intervening layers may also be present.

In the description, "

" means a connecting part.

In the description, the term "substituted or unsubstituted" corresponds to substituted or unsubstituted with at least one substituent selected from the group consisting of a deuterium atom, a halogen atom, a cyano group, a nitro group, an amino group, a silyl group, a boron group, a phosphine oxide group, a phosphine sulfide group, an oxy group, a thio group, a sulfoxy group, an alkyl group, an alkenyl group, an aryl group, and a heterocyclic group. In addition, each of the substituents may be substituted or unsubstituted. For example, the biphenyl group may be interpreted as an aryl group or a phenyl group substituted with a phenyl group.

In the description, the halogen may include a fluorine atom, a chlorine atom, a bromine atom and an iodine atom.

In the description, the alkyl group may be a linear, branched or cyclic type. The carbon number of the alkyl group may be from 1 to 30, from 1 to 20, from 1 to 15, from 1 to 10, or from 1 to 6. The alkyl group may include methyl, ethyl, n-propyl, isopropyl, n-butyl, s-butyl, t-butyl, t-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the description, the aryl group means an optional functional group or substituent derived from an aromatic hydrocarbon ring. The aryl group may be a monocyclic aryl group or a polycyclic aryl group. The carbon number for forming a ring in the aryl group may be 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylene, pyrenyl, benzofluoranthenyl, chrysenyl, etc., without limitation.

In the description, the fluorenyl group may be substituted, and two substituents may combine to each other to form a spiro structure.

In the description, the heteroaryl may be a heteroaryl including at least one of O, N, P, Si or S as a heteroatom. The carbon number for forming a ring of the heteroaryl may be 2 to 30, or 2 to 20. Examples of the heteroaryl may include thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidinyl, pyrido pyrazinyl, pyrazino pyrazinyl, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophene, thienothiophene, benzofuranyl, phenanthroline, thiazolyl, isooxazolyl, oxadiazolyl, thiadiazolyl, benzothiazolyl, phenothiazinyl, dibenzosilole, dibenzofuranyl, etc., without limitation.

In the description, explanation on the aryl may be applied to the arylene except that the aryl is a divalent group.

In the description, the silyl may include alkyl silyl and aryl silyl. Examples of the silyl may include trimethylsilyl, triethylsilyl, t-butyldimethylsilyl, vinyldimethylsilyl, propyldimethylsilyl, triphenylsilyl, diphenylsilyl, phenylsilyl, etc., without limitation.

In the description, the boron group may include an alkyl boron group and an aryl boron group. Examples of the boron group may include a trimethylboron group, a triethylboron group, a t-butyldimethylboron group, a triphenylboron group, a diphenylboron group, a phenylboron group, etc., without limitation.

In the description, the alkenyl may be linear or branched. The carbon number is not specifically limited, and may be 2 to 30, 2 to 20, or 2 to 10. Examples of the alkenyl may include vinyl, 1-butenyl, 1-pentenyl, 1,3-butadienylaryl, styrenyl, styrylvinyl, etc., without limitation.

In the description, the carbon number of the amino group is not specifically limited, and may be 1 to 30. The amino group may include an alkylamino group and an arylamino group. Examples of the amino group may include a methylamino group, a dimethylamino group, a phenylamino group, a diphenylamino group, a naphthylamino group, a 9-methyl-anthracenylamino group, a triphenylamino group, etc., without limitation.

In the description, the carbon number of the carbonyl group is not specifically limited, and may be 1 to 40, 1 to 30, or 1 to 20. For example, the carbonyl may have the following structure, but is not limited thereto.

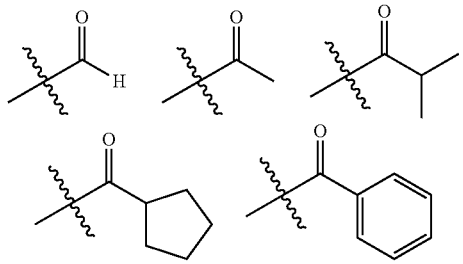

In the description, the carbon number of the sulfoxy group is not specifically limited, and may be 1 to 30. The sulfoxy group may include an alkyl sulfoxy group and an aryl sulfoxy group. Examples of the sulfoxy group may include a methylsulfoxy group, a dimethylsulfoxy group, a trifluoromethylsulfoxy group, a nitrobenzenylsulfoxy group, a tolylsulfoxy group, etc., without limitation.

In the description, the thio group may include an alkyl thio group and an aryl thio group.

In the description, the oxy group may include an alkoxy group and an aryloxy group. The alkoxy group may be a linear, a branched or a cyclic branch. The carbon number of the alkoxy group is not specifically limited and may be 1 to 20, or 1 to 10. Examples of the alkoxy group may include methoxy, ethoxy, n-propoxy, isopropoxy, butoxy, pentyloxy, hexyloxy, octyloxy, nonyloxy, decyloxy, benzyloxy, etc., without limitation.

In the description, the alkyl group in alkylthio, alkylsulfoxy, alkylaryl, alkylamino, alkylboron, and alkylsilyl may be the same as the alkyl group described above.

In the description, the aryl group in aryloxy, arylthio, arylsulfoxy, arylamino, arylboron, and arylsilyl may be the same as the aryl group described above.

Hereinafter, a polycyclic compound according to an embodiment will be explained.

A polycyclic compound according to an embodiment is represented by the following Formula 1.

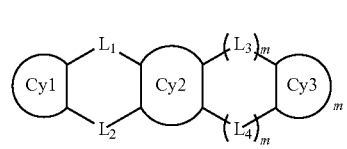

[Formula 1]

In Formula 1 according to an example embodiment, Cy1 to Cy3 may each independently be a substituted or unsubstituted five-membered heteroaryl group, or a substituted or unsubstituted six-membered aryl group. In an example embodiment, at least one of Cy1 or Cy2 may be the substituted or unsubstituted five-membered heteroaryl group.

In an example embodiment, Cy1 to Cy3 may each independently be represented by the following Formula 2-1 or 2-2. In an example embodiment, one of Cy1 or Cy2 may be represented by Formula 2-2.

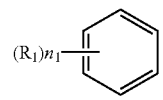

[Formula 2-1]

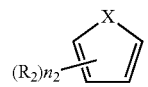

[Formula 2-2]

In an example embodiment, in Formulae 2-1 and 2-2,
X may be one of O, S, or $NY_1$.

$Y_1$ may be a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted boron group, a substituted or unsubstituted sulfoxy group, a substituted or unsubstituted phosphine oxide group, a substituted or unsubstituted carbonyl group, or a substituted or unsubstituted silyl group. $Y_1$ may be a substituted or unsubstituted aryl group having 6 to 15 carbon atoms. For example, $Y_1$ may be a substituted or unsubstituted phenyl group. $Y_1$ may be the unsubstituted phenyl group.

$R_1$ and $R_2$ may each independently be a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted oxy group, a substituted or unsubstituted thio group, a substituted or unsubstituted boron group, a substituted or unsubstituted sulfoxy group, a substituted or unsubstituted phosphine oxide group, a substituted or unsubstituted carbonyl group, a substituted or unsubstituted amino group, or a substituted or unsubstituted silyl group. $R_1$ and $R_2$ may each independently be a substituted or unsubstituted aryl group having 6 to 15 carbon atoms for forming a ring, or a substituted or unsubstituted silyl group. $R_1$ and $R_2$ may each independently be a substituted or unsubstituted aryl silyl group. For example, $R_1$ and $R_2$ may each independently be a substituted or unsubstituted phenyl group, or a substituted or unsubstituted triphenylsilyl group.

$R_1$ and $R_2$ may be the same or different. For example, both $R_1$ and $R_2$ may be an unsubstituted phenyl group.

$n_1$ may be an integer of 0 to 4. In the case where $n_1$ is an integer of 2 or more, a plurality of $R_1$ may be the same or different. $n_2$ may be an integer of 0 to 2. In the case where $n_2$ is 2, a plurality of $R_2$ may be the same or different.

$L_1$ to $L_4$ may each independently be a substituted or unsubstituted divalent alkyl group having 1 to 10 carbon atoms, a substituted or unsubstituted divalent amino group, a substituted or unsubstituted divalent oxy group, a substituted or unsubstituted divalent thio group, a substituted or unsubstituted divalent sulfoxy group, a substituted or unsubstituted divalent phosphine oxide group, or a substituted or unsubstituted divalent silyl group.

$L_1$ to $L_4$ may each independently be a substituted or unsubstituted divalent alkyl group having 1 to 10 carbon atoms, a substituted or unsubstituted divalent silyl group, a substituted or unsubstituted divalent oxy group, or a substituted or unsubstituted divalent thio group.

$L_1$ to $L_4$ may each independently be substituted with a substituted or unsubstituted aryl group having 6 to 15 carbon atoms for forming a ring. For example, $L_1$ to $L_4$ may each independently be a divalent alkyl group having 1 to 10 carbon atoms and substituted with a substituted or unsubstituted aryl group having 6 to 15 carbon atoms for forming a ring. $L_1$ to $L_4$ may each independently be a divalent methyl group, substituted with a substituted or unsubstituted phenyl group.

$L_1$ to $L_4$ may each independently be $CY_2Y_3$, $NY_4$, $SiY_5Y_6$, O or S. $Y_2$ to $Y_6$ may each independently be a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted boron group, a substituted or unsubstituted sulfoxy group, a substituted or unsubstituted phosphine oxide group, a substituted or unsubstituted carbonyl group, or a substituted or unsubstituted silyl group. $Y_2$ to $Y_6$ may each independently be a substituted or unsubstituted aryl group having 6 to 15 carbon atoms.

$L_1$ to $L_4$ may be the same or different. For example, all $L_1$ to $L_4$ may be a divalent methyl group substituted with an unsubstituted phenyl group.

m may be 0 or 1. In the case where m is 0, the polycyclic compound according to an embodiment may be a three-membered compound in which Cy1 and Cy2 are connected via $L_1$ and $L_2$. In the case where m is 1, the polycyclic compound according to an embodiment may be a five-membered compound in which Cy1 and Cy2 are connected via $L_1$ and $L_2$, and Cy2 and Cy3 are connected via $L_3$ and $L_4$.

In the case where m is 1, Cy1 to Cy3 may be the same or different. For example, Cy1 and Cy3 may be represented by Formula 2-1, and Cy2 may be represented by Formula 2-2, Cy1 and Cy3 may be represented by Formula 2-2, and Cy2 may be represented by Formula 2-1, etc.

In the case where m is 0, Cy1 and Cy2 may be the same or different. For example, Cy1 may be represented by Formula 2-1 and Cy2 may be represented by Formula 2-2, both Cy1 and Cy2 may be represented by Formula 2-2, etc.

The polycyclic compound represented by Formula 1 may be represented by one of the following Formulae 3-1 to 3-4.

[Formula 3-1]

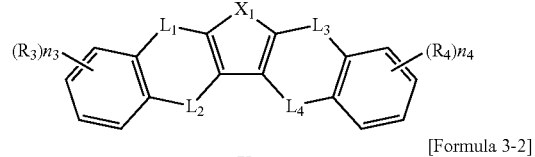

[Formula 3-2]

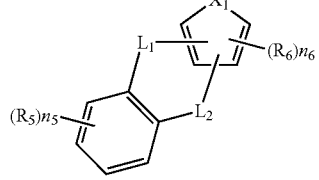

[Formula 3-3]

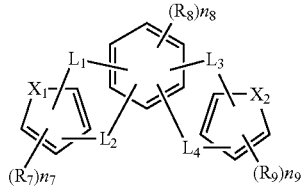

[Formula 3-4]

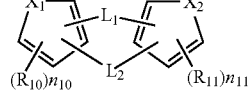

Particular explanation on $L_1$ to $L_4$ may be the same as that explained in Formula 1.

$X_1$ and $X_2$ may each independently be one of O, S, or $NY_1$. $X_1$ and $X_2$ may be the same or different. Particular explanation on $Y_1$ may be the same as that explained in Formula 1.

$R_3$ to $R_{11}$ may each independently be a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted alkoxy group, a substituted or unsubstituted aryl oxy group, a substituted or unsubstituted alkyl thio group, a substituted or unsubstituted aryl thio group, a substituted or unsubstituted boron group, a substituted or unsubstituted sulfoxy group, a substituted or unsubstituted phosphine oxide group, a substituted or unsubstituted carbonyl group, a substituted or unsubstituted amino group, or a substituted or unsubstituted silyl group. $R_3$ to $R_{11}$ may each independently be a substituted or unsubstituted aryl group having 6 to 15 carbon atoms for forming a ring.

$R_3$ to $R_{11}$ may be the same or different. In an example embodiment, all of $R_3$ to $R_{11}$ may be an unsubstituted phenyl group.

$n_3$ to $n_5$ may be an integer of 0 to 4, $n_6$ to $n_{11}$ may be an integer of 0 to 2.

In the case where $n_3$ is 2 or more, a plurality of $R_3$ may be the same or different. In the case where $n_4$ is 2 or more, a plurality of $R_4$ may be the same or different. In the case where $n_5$ is 2 or more, a plurality of $R_5$ may be the same or different. In the case where $n_6$ is 2 or more, a plurality of $R_6$ may be the same or different. In the case where $n_7$ is 2 or more, a plurality of $R_7$ may be the same or different. In the case where ng is 2 or more, a plurality of $R_8$ may be the same or different. In the case where $n_9$ is 2 or more, a plurality of $R_9$ may be the same or different. In the case where $n_{10}$ is 2 or more, a plurality of $R_{10}$ may be the same or different. In the case where $n_{11}$ is 2 or more, a plurality of $R_{11}$ may be the same or different.

The polycyclic compound represented by Formula 3-2 may be represented by the following Formula 3-2-1 or 3-2-2.

[Formula 3-2-1]

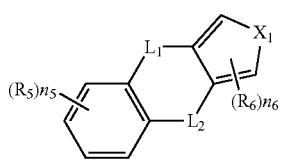

[Formula 3-2-2]

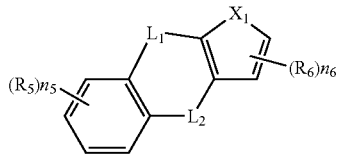

In Formulae 3-2-1 and 3-2-2, $L_1$, $L_2$, $R_5$, $R_6$, $X_1$, $n_5$ and $n_6$ are the same as defined above.

The polycyclic compound represented by Formula 3-3 may be represented by one of the following Formula 3-3-1 or 3-3-2.

[Formula 3-3-1]

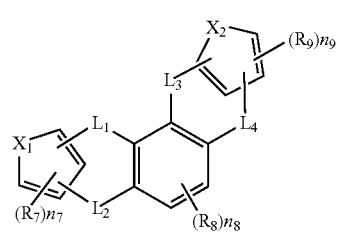

[Formula 3-3-2]

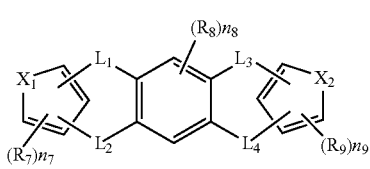

$L_1$, $L_2$, $L_3$, $L_4$, $R_7$, $R_8$, $R_9$, $X_1$, $X_2$, $n_7$, $n_8$ and $n_9$ are the same as defined above.

The polycyclic compound represented by Formula 3-3-1 may be represented by one of the following Formulae 3-3-1-1 to 3-3-1-3.

[Formula 3-3-1-1]

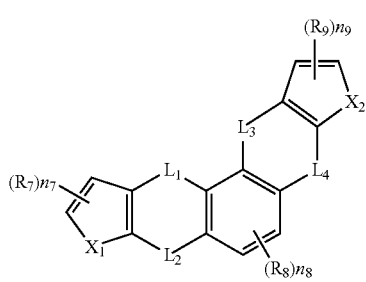

[Formula 3-3-1-2]

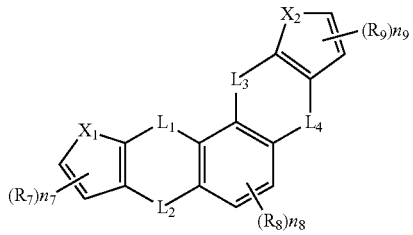

[Formula 3-3-1-3]

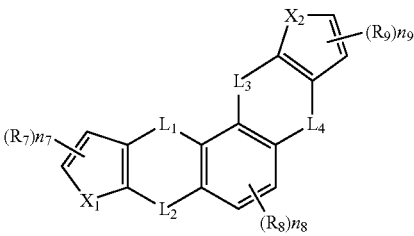

$L_1$, $L_2$, $L_3$, $L_4$, $R_7$, $R_8$, $R_9$, $X_1$, $X_2$, $n_7$, $n_8$ and $n_9$ are the same as defined above.

The polycyclic compound represented by Formula 3-3-2 may be represented by the following Formula 3-3-2-1 or 3-3-2-2.

[Formula 3-3-2-1]

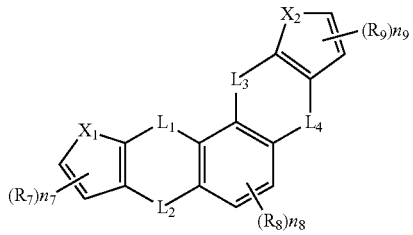

[Formula 3-3-2-1]

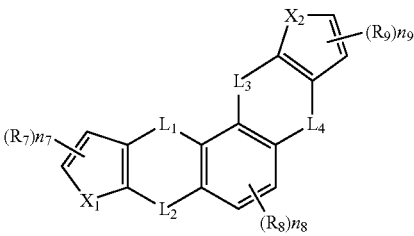

$L_1$, $L_2$, $L_3$, $L_4$, $R_7$, $R_8$, $R_9$, $X_1$, $X_2$, $n_7$, $n_8$ and $n_9$ are the same as defined above.

The polycyclic compound represented by Formula 3-4 may be represented by the following Formula 3-4-1 or 3-4-2.

[Formula 3-4-1]

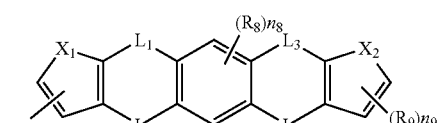

[Formula 3-4-2]

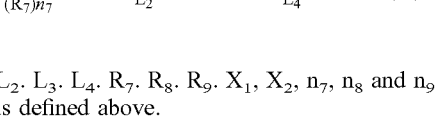

$L_1$, $L_2$, $R_{10}$, $R_{11}$, $X_1$, $X_2$, $n_{10}$ and $n_{11}$ are the same as defined above.

The polycyclic compound represented by Formula 1 may be one selected from the compounds represented in the following Compound Group 1. However, an embodiment is not limited thereto.
[Compound Group 1]
1
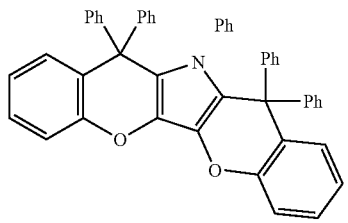
2
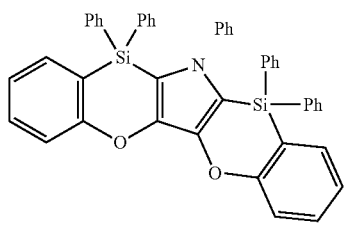
3
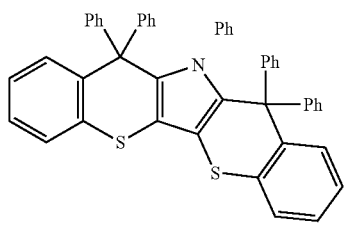
4
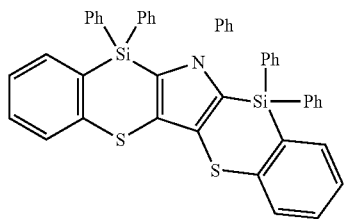
5
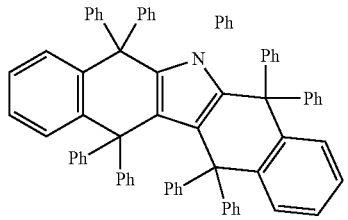
6
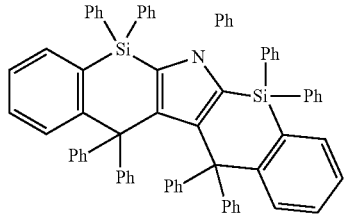
-continued
7
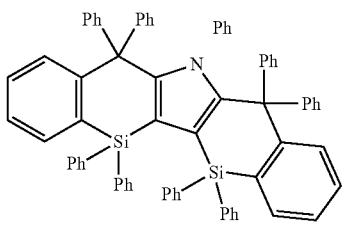
8
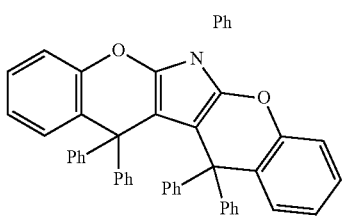
9
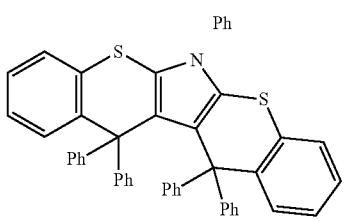
10
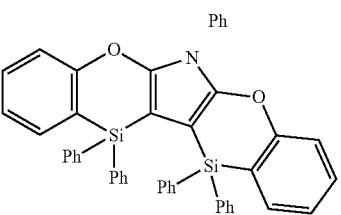
11
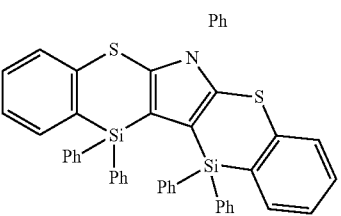
12
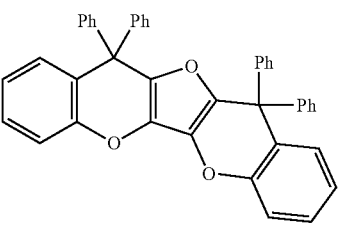
13
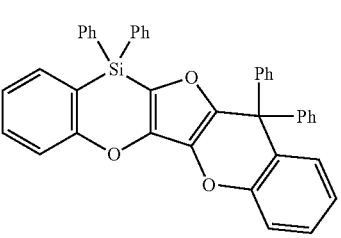

14
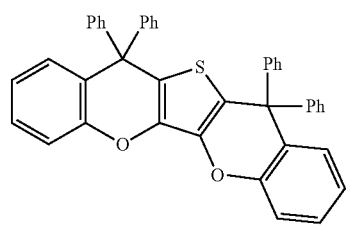
15
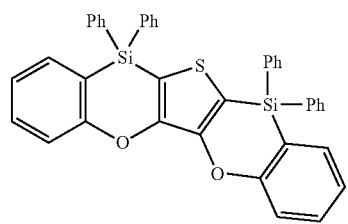
16
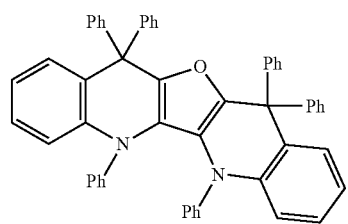
17
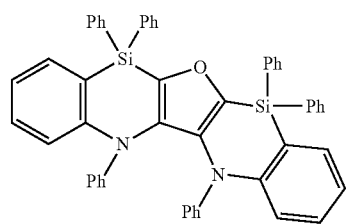
18
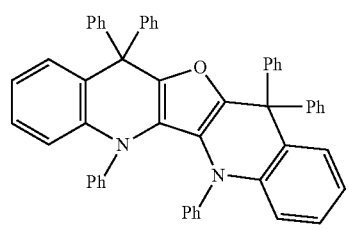
19
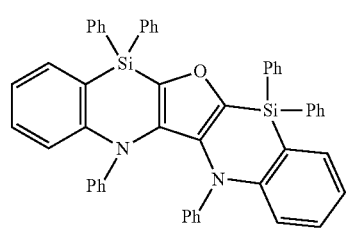
20
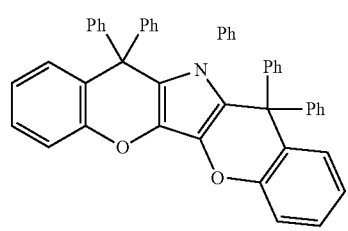
21
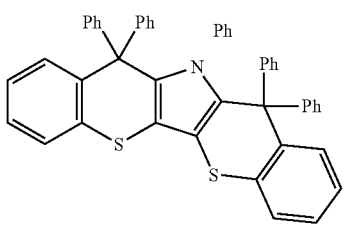
22
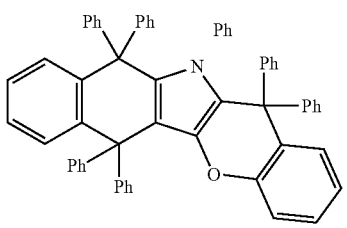
23
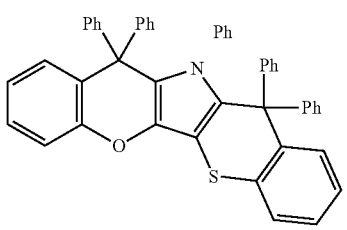
24
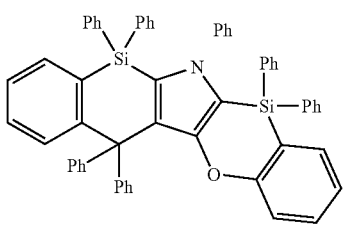
25
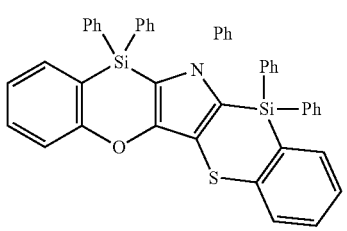
26
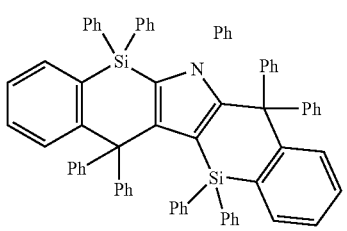
27
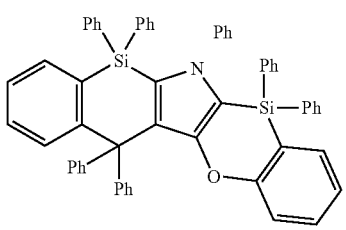

-continued
28
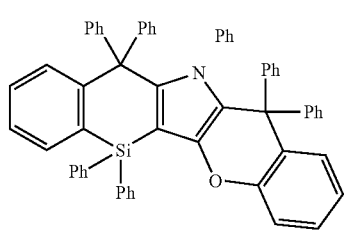
29
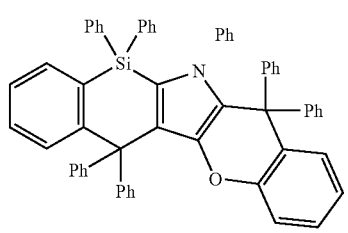
30
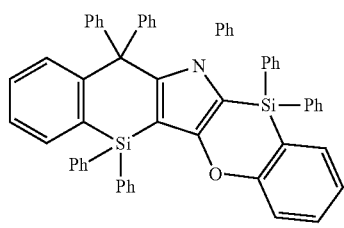
31
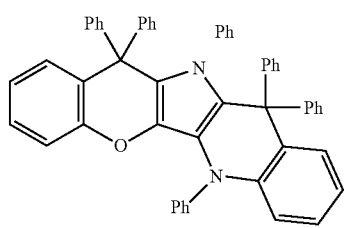
32
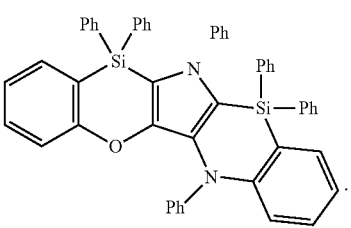
The polycyclic compound represented by Formula 1 may be one selected from the compounds represented in the following Compound Group 2. However, an embodiment is not limited thereto.
[Compound Group 2]
33
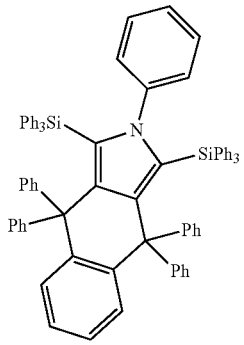
34
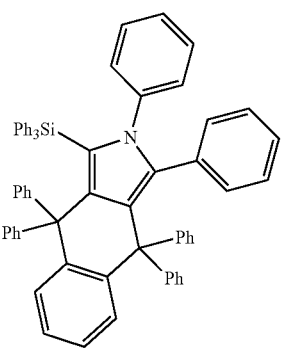
35
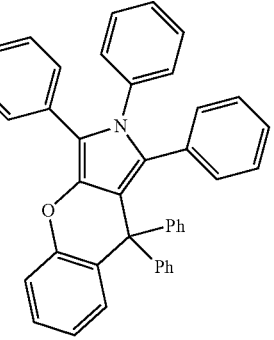
36
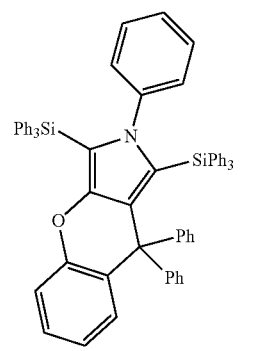

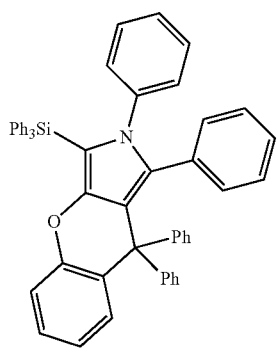
37
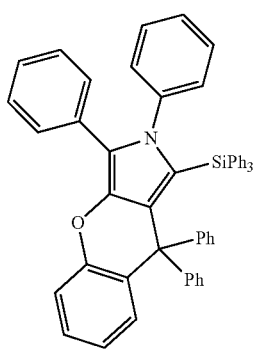
38
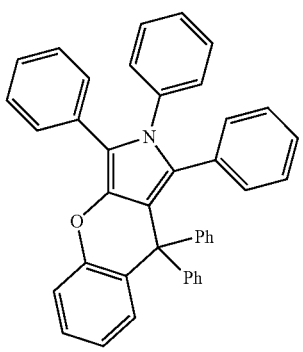
39
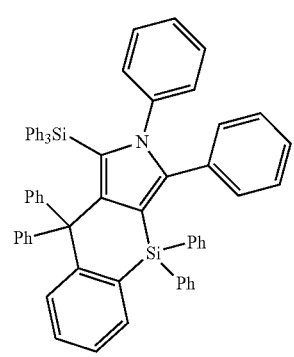
40
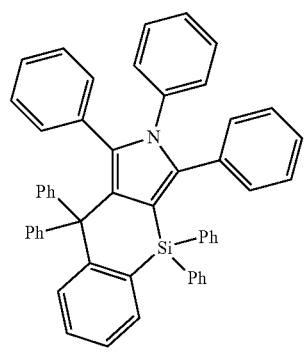
41
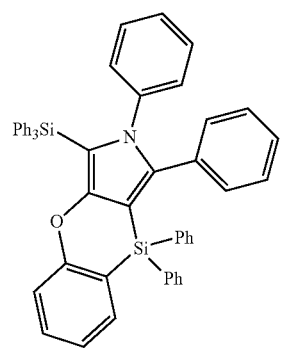
42
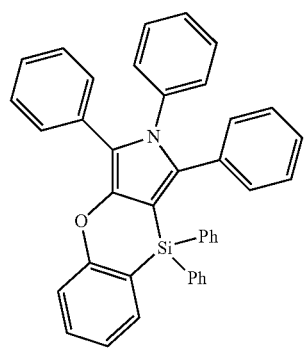
43
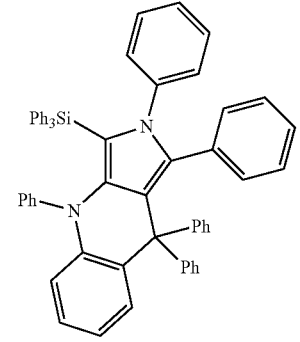
44

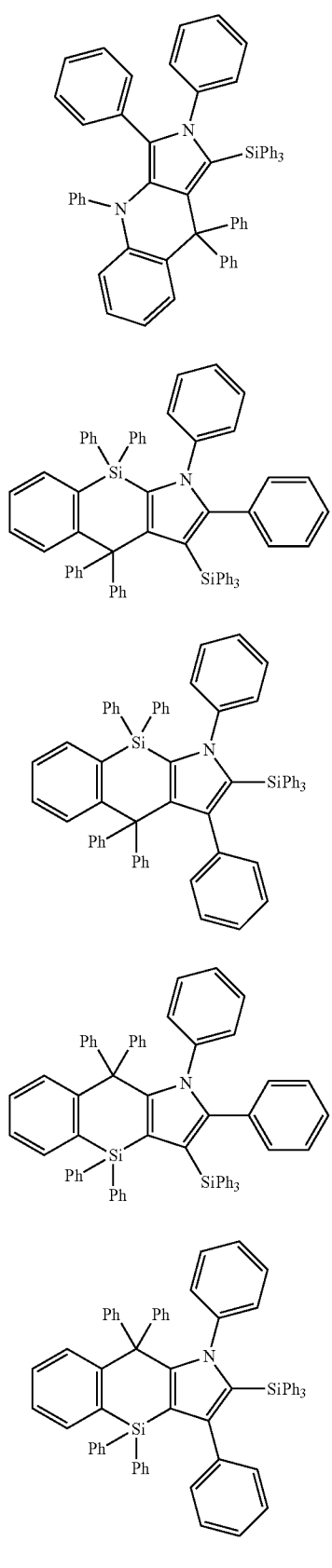
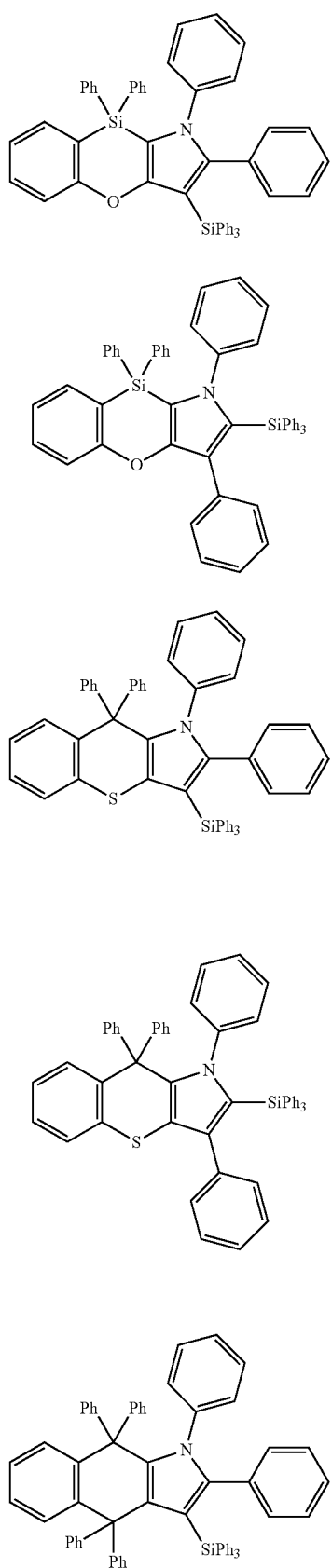

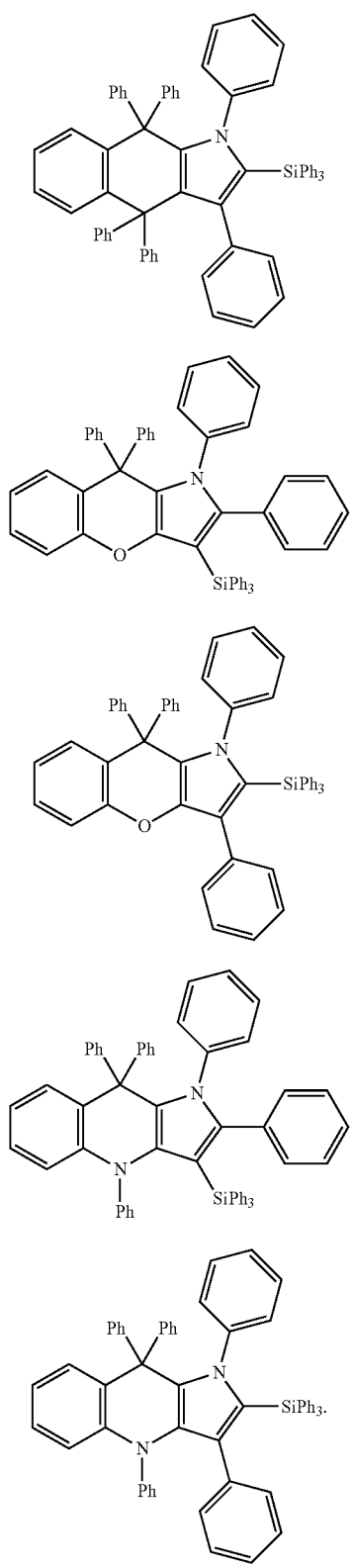
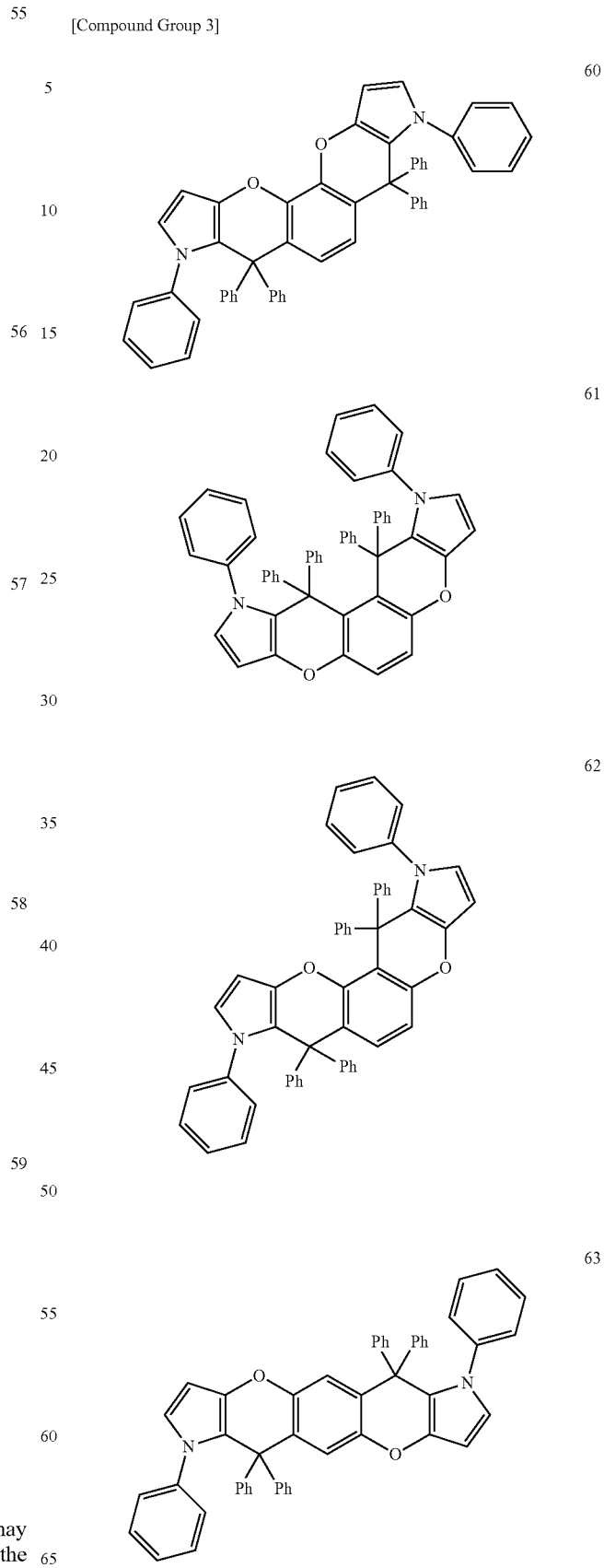
[Compound Group 3]
The polycyclic compound represented by Formula 1 may be one selected from the compounds represented in the following Compound Group 3. However, an embodiment is not limited thereto.

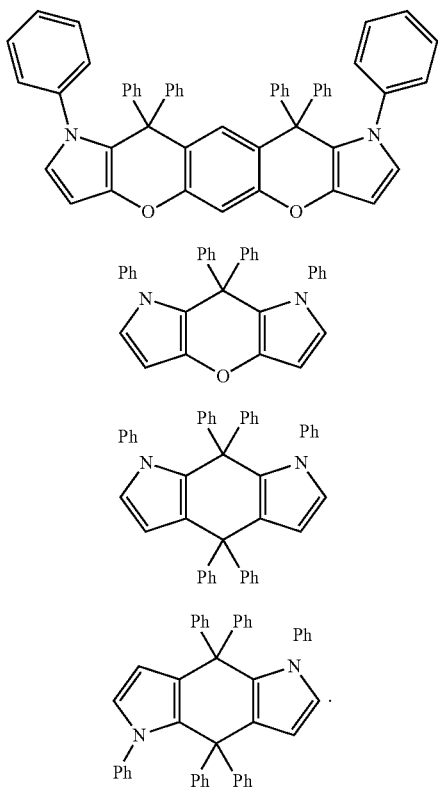

The polycyclic compound according to an embodiment has a structure represented by Formula 1. When the polycyclic compound according to an embodiment is applied to an organic electroluminescence device, high emission efficiency may be secured.

The polycyclic compound represented by Formula 1 has a structure in which a five-membered heteroaryl group and an aromatic hydrocarbon ring are not directly condensed, which may help provide a high triplet energy level. When the polycyclic compound represented by Formula 1 is used as a material for a hole transport layer which is adjacent to an emission layer, the diffusion of triplet excitons generated in the emission layer toward a hole transport region may be suppressed, which may help provide high emission efficiency of an organic electroluminescence device.

Hereinafter, an organic electroluminescence device according to an embodiment will be described. Hereinafter, different features from the above-described polycyclic compound according to an embodiment will be mainly explained in particular, and unexplained parts will follow the explanation on the polycyclic compound according to an embodiment.

An organic electroluminescence device according to an embodiment includes the above-described polycyclic compound according to an embodiment.

Figure 2:
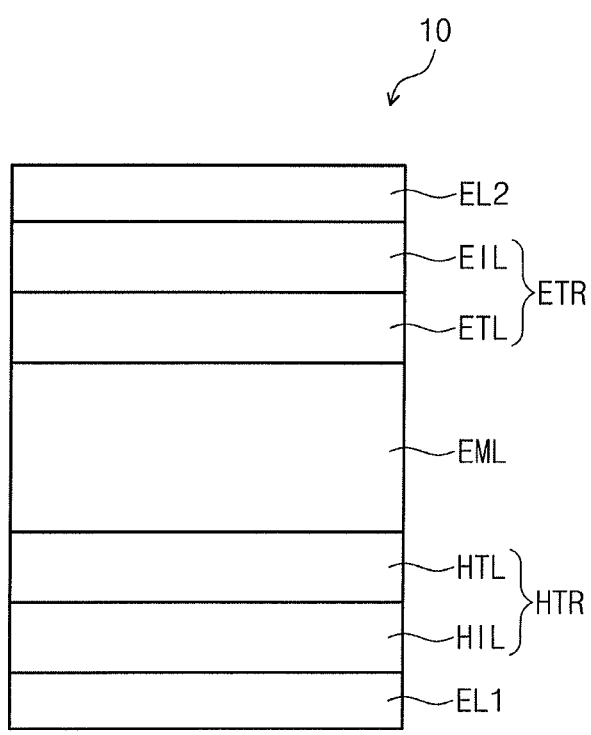
FIG. 2 illustrates a cross-sectional view schematically illustrating an organic electroluminescence device according to an embodiment.
Figure 3:
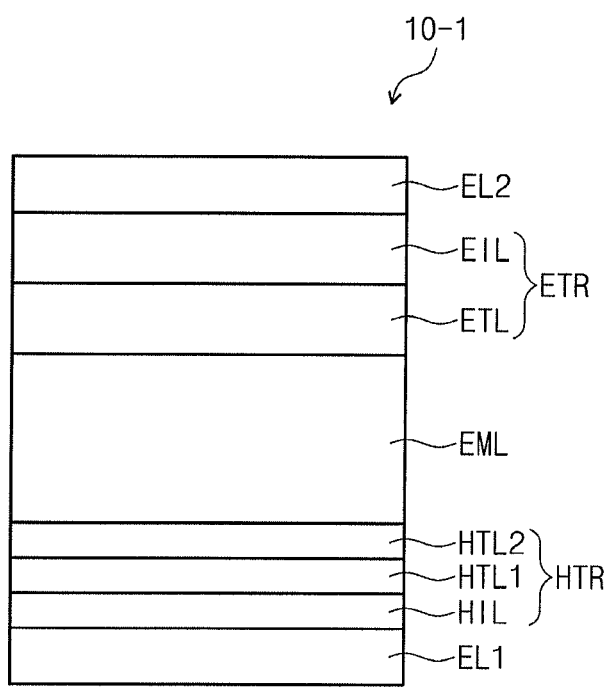
FIG. 3 illustrates a cross-sectional view schematically illustrating an organic electroluminescence device according to an embodiment.

FIG. 1 is a cross-sectional view schematically illustrating an organic electroluminescence device according to an embodiment. FIG. 2 is a cross-sectional view schematically illustrating an organic electroluminescence device according to an embodiment. FIG. 3 is a cross-sectional view schematically illustrating an organic electroluminescence device according to an embodiment.

Referring to FIGS. 1 to 3, an organic electroluminescence device 10 according to an embodiment includes a first electrode EL1, a hole transport region HTR, an emission layer EML, an electron transport region ETR, and a second electrode EL2.

The first electrode EL1 has conductivity. The first electrode EL1 may be, for example, a pixel electrode or an anode. The first electrode EL1 may be, for example, a transmissive electrode, a transflective electrode, or a reflective electrode. In the case where the first electrode EL1 is the transmissive electrode, the first electrode EL1 may be formed using, for example, a transparent metal oxide such as indium tin oxide (ITO), indium zinc oxide (IZO), zinc oxide (ZnO), and indium tin zinc oxide (ITZO). In the case where the first electrode EL1 is the transflective electrode or the reflective electrode, the first electrode EL1 may include, for example, Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may include, for example, a plurality of layers including a reflective layer or a transflective layer formed using the above materials, and a transmissive layer formed using, for example, ITO, IZO, ZnO, or ITZO.

Hereinafter, an embodiment in which the polycyclic compound according to an embodiment is included in the electron transport region ETR will be explained. However, the inventive concept is not limited thereto. The polycyclic compound according to an embodiment may be included in at least one layer of the plurality of the organic layers disposed between the first electrode EL and the second electrode EL2.

The organic electroluminescence device according to an embodiment includes the polycyclic compound represented by Formula 1 in, for example, a hole transport region HTR. The hole transport region HTR may include one kind or two or more kinds of the polycyclic compound represented by Formula 1.

[Formula 1]

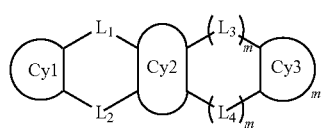

In Formula 1, the explanation on $L_t$ to $L_4$, m, Cy1 to Cy3 is the same as described above, and particular explanation thereon will be omitted.

The above-description may be applied to the particular explanation on the polycyclic compound represented by Formula 1, and thus, the particular explanation thereon will be omitted.

The hole transport region HTR may be provided on the first electrode EL1. The hole transport region HTR may include, for example, at least one of a hole injection layer HIL, a hole transport layer HTL, a hole buffer layer, or an electron blocking layer. The thickness of the hole transport region HTR may be, for example, from about 1,000 Å to about 1,500 Å.

The hole transport region HTR may have, for example, a single layer formed using a single material, a single layer formed using a plurality of different materials, or a multi-layer structure including a plurality of layers formed using a plurality of different materials.

For example, as shown in FIG. 2, the hole transport region HTR may have the structure of a single layer such as a hole injection layer HIL, or a hole transport layer HTL, and may have a structure of a single layer formed using a hole injection material and a hole transport material. In addition, the hole transport region HTR may have a structure of a single layer formed using a plurality of different materials, or a structure laminated from the first electrode EL 1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer, without limitation.

As shown in FIG. 3, the hole transport region HTR may include a plurality of hole transport layers. The hole transport region HTR may include a first hole transport layer HTL1 and a second hole transport layer HTL2 disposed on the first hole transport layer HTL1. The second hole transport layer HTL2 among the plurality of hole transport layers may be a hole transport layer adjacent to the emission layer EML.

The hole transport region HTR may be formed using, for example, various methods such as a vacuum deposition method, a spin coating method, a cast method, a Langmuir-Blodgett (LB) method, an inkjet printing method, a laser printing method, and a laser induced thermal imaging (LITI) method.

The hole transport region HTR may include the polycyclic compound according to an embodiment as a hole transport material. A layer including the polycyclic compound according to an embodiment may be a hole transport layer HTL. In the case where the hole transport layer includes a first hole transport layer HTL1 and a second hole transport layer HTL2 as shown in FIG. 3, the polycyclic compound according to an embodiment may be included in, for example, the second hole transport layer HTL2. The polycyclic compound according to an embodiment may be included in a layer adjacent to the emission layer EML among the hole transport region HTR.

In the case where the hole transport region HTR includes the polycyclic compound according to an embodiment, the hole injection material may include, for example, a phthalocyanine compound such as copper phthalocyanine, N,N'-diphenyl-N,N'-bis-[4-(phenyl-m-tolyl-amino)-phenyl]-biphenyl-4,4'-diamine (DNTPD), 4,4',4"-tris(3-methylphenylphenylamino)triphenylamine (m-MTDATA), 4,4',4"-tris(N,N-diphenylamino)triphenylamine (TDATA), 4,4',4"-tris {N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(1-naphthalene-1-yl)-N,N'-diphenyl-benzidine (NPB), triphenylamine-containing polyetherketone (TPAPEK), 4-isopropyl-4'-methyldiphenyliodonium, tetrakis(pentafluorophenyl)borate]hexaazatriphenylenehexacarbonitrile (HAT-CN), etc.

In the case where the hole transport layer HTL does not include the polycyclic compound according to an embodiment, for example, in the case where the electron blocking layer includes the polycyclic compound according to an embodiment, the hole transport layer may include, for example, carbazole derivatives such as N-phenyl carbazole and polyvinyl carbazole, fluorine derivatives, N,N'-bis(3-methylphenyl)-N,N'-diphenyl-[1,1-biphenyl]-4,4'-diamine (TPD), triphenylamine derivatives such as 4,4',4"-tris(N-carbazolyl)triphenylamine (TCTA), N,N'-di(1-naphthyl)-N, N'-diphenylbenzidine (NPB), 4,4'-cyclohexylidene bis[N,N-bis(4-methylphenyl)benzenamine (TAPC), 4,4'-bis[N,N'-(3-tolyl)amino]-3,3'-dimethylbiphenyl (HMTPD), etc.

The thickness of the hole transport region HTR may be, for example, from about 100 Å to about 10,000 Å, for example, from about 100 Å to about 1,000 Å. In the case where the hole transport region HTR includes both the hole injection layer HIL and the hole transport layer HTL, the thickness of the hole injection layer HIL may be, for example, from about 100 Å to about 10,000 Å, for example, from about 100 Å to about 1,000 Å, and the thickness of the hole transport layer HTL may be, for example, from about 30 Å to about 1,000 Å. In the case where the thicknesses of the hole transport region HTR, the hole injection layer HIL, and the hole transport layer HTL satisfy the above-described ranges, satisfactory hole transport properties may be obtained without substantial increase of a driving voltage.

The hole transport region HTR may further include, for example, a charge generating material other than the above-described materials to improve conductivity. The charge generating material may be dispersed uniformly or non-uniformly in the hole transport region HTR. The charge generating material may be, for example, a p-dopant. The p-dopant may be, for example, one of quinone derivatives, metal oxides, or cyano group-containing compounds, without limitation. For example, non-limiting examples of the p-dopant may include quinone derivatives such as tetracyanoquinodimethane (TCNQ), and 2,3,5,6-tetrafluoro-tetracyanoquinodimethane (F4-TCNQ), metal oxides such as tungsten oxide, and molybdenum oxide, without limitation.

As described above, the hole transport region HTR may further include one of a hole buffer layer and an electron blocking layer in addition to the hole injection layer HIL and the hole transport layer HTL. The hole buffer layer may compensate an optical resonance distance according to the wavelength of light emitted from the emission layer EML and increase light emission efficiency. Materials included in the hole transport region HTR may be used as materials included in the hole buffer layer. The electron blocking layer may be a layer preventing electron injection from the electron transport region ETR to the hole transport region HTR.

The emission layer EML may be provided on the hole transport region HTR. The thickness of the emission layer EML may be, for example, from about 100 Å to about 300 Å. The emission layer EML may have, for example, a single layer formed using a single material, a single layer formed using a plurality of different materials, or a multilayer structure having a plurality of layers formed using a plurality of different materials.

The emission layer EML may emit, for example, one of red light, green light, blue light, white light, yellow light, or cyan light. The emission layer EML may include, for example, a phosphorescent material or a fluorescent material. The emission layer EML may include, for example, a host and a dopant. The emission layer EML may have a thickness of, for example, about 10 to about 60 nm.

The host may be or include, without specific limitation, for example, tris(8-hydroxyquinolino)aluminum ($Alq_3$), 4,4'-bis(N-carbazolyl)-1,1'-biphenyl (CBP), poly(n-vinylcarbazole) (PVK), 9,10-di(naphth-2-yl)anthracene (ADN), 4,4',4"-tris(carbazol-9-yl)-triphenylamine (TCTA), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphth-2-yl)anthracene (MADN), 1,3-bis(N-carbazolyl)benzene (mCP), etc.

The dopant may include, for example, styryl derivatives (for example, 1,4-bis[2-(3-N-ethylcarbazolyl)vinyl]benzene (BCzVB), 4-(di-p-tolylamino)-4'-[(di-p-tolylamino)styryl]

stilbene (DPAVB), N-(4-((E)-2-(6-((E)-4-(diphenylamino) styryl)naphthalen-2-yl)vinyl)phenyl)-N-phenylbenzenamine (N-BDAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, 1,4-bis(N,N-diphenylamino)pyrene), etc.

When the emission layer EML emits red light, the emission layer EML may include, for example, tris(dibenzoylmethanato)phenanthroline europium (PBD:Eu(DBM)$_3$ (Phen)), or a phosphorescent material including perylene. In the case that the emission layer EML emits red light, the dopant included in the emission layer EML may be selected from, for example, a metal complex or an organometallic complex such as bis(1-phenylisoquinoline)acetylacetonate iridium (PIQIr(acac)), bis(1-phenylquinoline)acetylacetonate iridium (PQIr(acac), tris(1-phenylquinoline)iridium (PQIr), and octaethylporphyrin platinum (PtOEP), rubrene and the derivatives thereof, or 4-dicyanomethylene-2-(p-dimethylaminostyryl)-6-methyl-4H-pyran (DCM) and the derivatives thereof.

In the case where the emission layer EML emits green light, the emission layer EML may include, for example, a phosphorescent material including, for example, tris(8-hydroxyquinolino)aluminum (Alq$_3$). In the case where the emission layer EML emits green light, the dopant included in the emission layer EML may be selected from, for example, a metal complex or organometallic complex such as fac-tris(2-phenylpyridine)iridium (Ir(ppy)$_3$), or coumarin and the derivatives thereof.

In the case that the emission layer EML emits blue light, the emission layer EML may include, for example, a phosphorescent material including at least one selected from the group of, for example, spiro-DPVBi, spiro-6P, distyrylbenzene (DSB), distyryl-arylene (DSA), a polyfluorene (PFO)-based polymer, and a poly(p-phenylene vinylene) (PPV)-based polymer. In the case where the emission layer EML emits blue light, the dopant included in the emission layer EML may be selected from, for example, a metal complex or an organometallic complexes such as bis[2-(4, 6-difluorophenyl)pyridinato-C2,N](picolinato)iridium(III) (FIrpic), or perylene and the derivatives thereof.

The electron transport region ETR may be provided on the emission layer EML. The electron transport region ETR may include, for example, at least one of an electron blocking layer, an electron transport layer ETL or an electron injection layer EIL, without limitation.

The electron transport region ETR may have, for example, a single layer formed using a single material, a single layer formed using a plurality of different materials, or a multilayer structure having a plurality of layers formed using a plurality of different materials.

For example, the electron transport region ETR may have a single layer structure of the electron injection layer EIL or the electron transport layer ETL, or a single layer structure formed using an electron injection material and an electron transport material. In addition, the electron transport region ETR may have a single layer structure having a plurality of different materials, or a structure laminated from the first electrode EL1 of electron transport layer ETL/electron injection layer EIL, or hole blocking layer/electron transport layer ETL/electron injection layer EIL, without limitation. The thickness of the electron transport region ETR may be, for example, from about 1,000 Å to about 1,500 Å.

The electron transport region ETR may be formed using, for example, various methods such as a vacuum deposition method, a spin coating method, a cast method, a Langmuir-Blodgett (LB) method, an inkjet printing method, a laser printing method, and a laser induced thermal imaging (LITI) method.

In the case where the electron transport region ETR includes the electron transport layer ETL, the electron transport region ETR may include, for example, tris(8-hydroxyquinolinato)aluminum (Alq$_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,08)-(1,1'-biphenyl-4-olato) aluminum (BAlq), berylliumbis(benzoquinolin-10-olate (Bebq$_2$), 9,10-di(naphthalene-2-yl)anthracene (ADN), or a mixture thereof, without limitation. The thickness of the electron transport layer ETL may be, for example, from about 100 Å to about 1,000 Å and may be from about 150 Å to about 500 Å. If the thickness of the electron transport layer ETL satisfies the above-described range, satisfactory electron transport property may be obtained without substantial increase of a driving voltage.

When the electron transport region ETR includes the electron injection layer EIL, the electron transport region ETR may include, for example, a metal such as Al, Ag, Li, Mg and Ca and a mixture thereof. However, an embodiment is not limited thereto. For example, the electron injection layer EIL may use LiF, lithium quinolate (Liq), Li$_2$O, BaO, NaCl, CsF, a metal in lanthanides such as Yb, or a metal halide such as RbCl and RbI, without limitation. The electron injection layer EIL also may be formed using a mixture material of an electron transport material and an insulating organo metal salt. The organo metal salt may be, for example, a material having an energy band gap of about 4 eV or more. The organo metal salt may include, for example, a metal acetate, a metal benzoate, a metal acetoacetate, a metal acetylacetonate, or a metal stearate. The thickness of the electron injection layer EIL may be, for example, from about 1 Å to about 100 Å, and from about 3 Å to about 90 Å. In the case where the thickness of the electron injection layer EIL satisfies the above described range, satisfactory electron injection properties may be obtained without inducing the substantial increase of a driving voltage.

The electron transport region ETR may include a hole blocking layer, as described above. The hole blocking layer may include, for example, at least one of, for example, 2,9-dimethyl-4,7-diphenyl-1,10-phenanthroline (BCP), or 4,7-diphenyl-1,10-phenanthroline (Bphen), without limitation.

The second electrode EL2 may be provided on the electron transport region ETR. The second electrode EL2 may be a common electrode or a cathode. The second electrode EL2 may be, for example, a transmissive electrode, a transflective electrode or a reflective electrode. In the case where the second electrode EL2 is the transmissive electrode, the second electrode EL2 may include a transparent metal oxide, for example, ITO, IZO, ZnO, ITZO, etc.

In the case where the second electrode EL2 is the transflective electrode or the reflective electrode, the second electrode EL2 may include, for example, Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

The second electrode EL2 may be connected with an auxiliary electrode. In the case where the second electrode EL2 is connected with the auxiliary electrode, the resistance of the second electrode EL2 may decrease.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes may recombine in the emission layer EML to generate excitons, and the excitons may emit light via transition from an excited state to a ground state.

In the case where the organic electroluminescence device 10 is a top emission type, the first electrode EL1 may be a reflective electrode, and the second electrode EL2 may be a transmissive electrode or a transflective electrode. In the case where the organic electroluminescence device 10 is a bottom emission type, the first electrode EL1 may be a transmissive electrode or a transflective electrode, and the second electrode EL2 may be a reflective electrode.

The organic electroluminescence device according to an embodiment includes a polycyclic compound represented by Formula 1 according to an embodiment, which may help secure high emission efficiency. The organic electroluminescence device according to an embodiment may include the polycyclic compound represented by Formula 1 in a hole transport region adjacent to an emission layer. In the case where the polycyclic compound represented by Formula 1 is used as a material for a hole transport layer which is adjacent to an emission layer, the diffusion of triplet excitons generated in the emission layer toward a hole transport region may be suppressed, which may help secure the high emission efficiency of an organic electroluminescence device.

A polycyclic compound according to an embodiment may be synthesized, for example, by the following. However, an embodiment is not limited thereto.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

SYNTHETIC EXAMPLES

1. Synthesis of Compound 1

(Synthesis of Compound A)

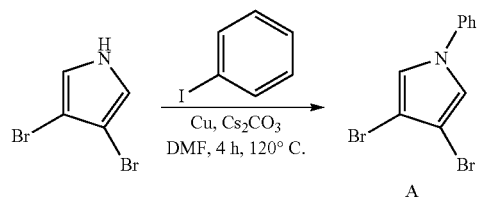

Under an argon (Ar) atmosphere, 13.5 g of 3,4-dibromopyrrole, 13.5 ml of iodobenzene, 0.384 g of a Cu powder, and 39.1 g of $Cs_2CO_3$ were added to a 300 ml, three-necked flask, and stirred in 120 ml of a dimethylformamide (DMF) solvent at about 120° C. for about 4 hours. After cooling in the air, toluene was added, and thus obtained product was filtered. Water was added to the filtrate, an organic layer was separated, and solvents were distilled. The crude product thus obtained was separated by column chromatography (using silica gel) to obtain 14.62 g of Compound A as a white solid (yield 81%). The molecular weight of Compound A measured by FAB-MS was 301.

(Synthesis of Compound B)

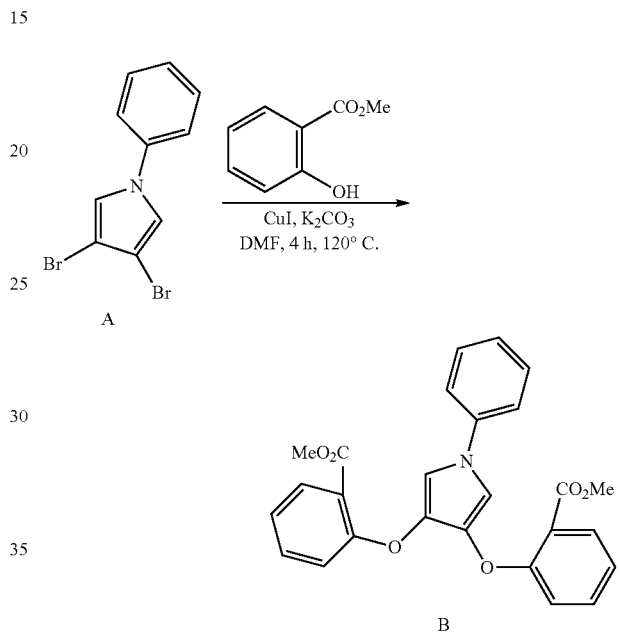

Under an argon (Ar) atmosphere, 7.31 g of Compound A, 9.5 ml of methyl salicylate, 0.93 g of CuI and 13.4 g of $K_2CO_3$ were added to a 300 ml, three-necked flask, and stirred in 100 ml of a DMF solvent at about 120° C. for about 4 hours. After cooling in the air, water and toluene were added, an organic layer was separated, and solvents were distilled. The crude product thus obtained was separated by column chromatography (using silica gel) to obtain 6.25 g of Compound B as a white solid (yield 58%).

The molecular weight of Compound B measured by FAB-MS was 443.

(Synthesis of Compound 1)

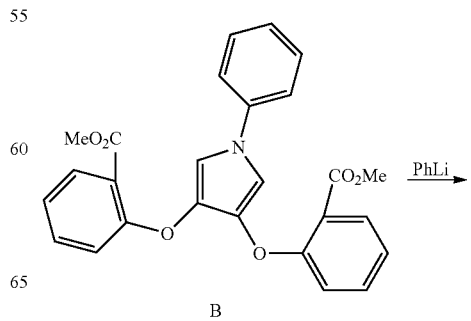

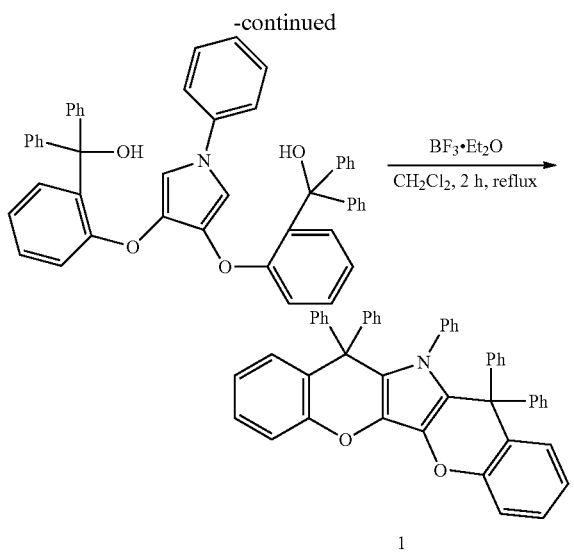

Under an argon (Ar) atmosphere, 6.2 ml of bromobenzene and 300 ml of an anhydrous tetrahydrofuran (THF) solution were added to a 1,000 ml three-necked flask and stirred at about −78° C. 37 ml of a hexane solution containing 1.6 M n-BuLi was added thereto dropwisely, followed by stirring for about 2 hours. 6.25 g of Compound B and 70 ml of an anhydrous THF solution were added thereto, followed by stirring at about −78° C. for about 2 hours and stirring at room temperature for about 3 hours. After the reaction, an aqueous solution of 1 N-hydrochloric acid was added thereto, followed by stirring for about 1 hour. The reactant was washed with water. The organic layer thus obtained was concentrated to obtain a viscous material. The viscous material, 300 ml of anhydrous dichloromethane, and 11 ml of BF$_3$·Et$_2$O were added to a 500 ml three-necked flask, and under an argon (Ar) atmosphere, heated and stirred at about 50° C. for about 2 hours for the reaction. After cooling in the air, water was added, an organic layer was separated, and solvents were distilled. The crude product thus obtained was separated by column chromatography (using silica gel) to obtain 2.96 g of Compound 1 as a white solid (yield 32%). The chemical shift values of the compound measured by $^1$H NMR were 7.63-7.57 (3H), 7.50 (2H), 7.26 (8H), 7.19-7.17 (6H), 7.10 (8H), 7.02-6.97 (4H), 6.85 (2H). In addition, the molecular weight of Compound 1 measured by FAB-MS was 655. From the results, the white solid compound was identified as Compound 1.

2. Synthesis of Compound 2

(Synthesis of Compound C)

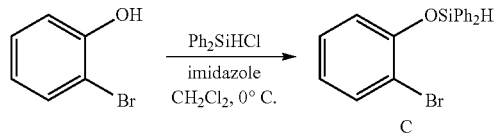

9.3 ml of 2-bromophenol, 17.6 ml of chlorodiphenylsilane, and 8.2 g of imidazole were added to a 300 ml, round-bottomed flask, and stirred in 160 ml of a dichloromethane solvent at about 0° C. for about 1 hour. After cooling in the air, water and dichloromethane were added, an organic layer was separated, and solvents were distilled. The crude product thus obtained was separated by recrystallization in ethanol to obtain 26.1 g of Compound C as a white solid (yield 92%). The molecular weight of Compound C measured by FAB-MS was 355.

(Synthesis of Compound D)

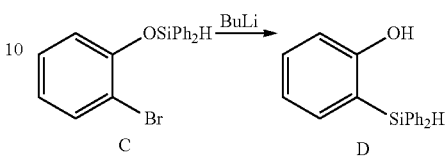

Under an argon (Ar) atmosphere, 26.1 g of Compound C. and 350 ml of an anhydrous THF solution were added to a 1,000 ml three-necked flask and stirred at about −78° C. 47 ml of a hexane solution containing 1.6 M n-BuLi was added thereto dropwisely, followed by stirring at about −78° C. for about 2 hours and stirring at room temperature for about 1 hour. The reactant was washed with water. The organic layer thus obtained was concentrated to obtain a viscous material. The viscous material thus obtained was separated by column chromatography (using silica gel) to obtain 17.26 g of Compound D as a white solid (yield 85%). The molecular weight of Compound D measured by FAB-MS was 276.

(Synthesis of Compound E)

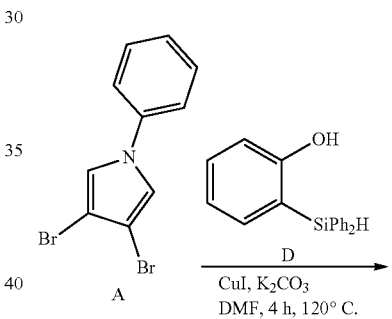

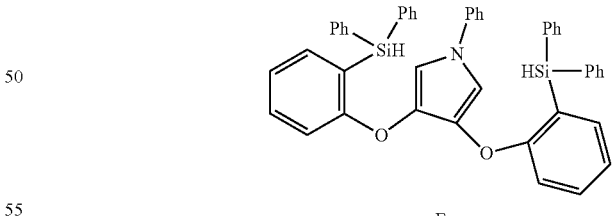

Under an argon (Ar) atmosphere, 7.31 g of Compound A, 13.8 g of Compound D, 0.93 g of CuI and 13.4 g of K$_2$CO$_3$ were added to a 300 ml, three-necked flask, and stirred in 100 ml of a DMF solvent at about 120° C. for about 4 hours. After cooling in the air, water and toluene were added, an organic layer was separated, and solvents were distilled. The crude product thus obtained was separated by column chromatography (using silica gel) to obtain 9.92 g of Compound E as a white solid (yield 59%). The molecular weight of Compound E measured by FAB-MS was 691.

(Synthesis of Compound 2)

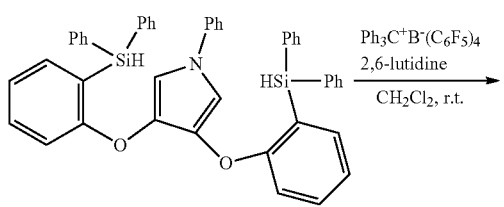

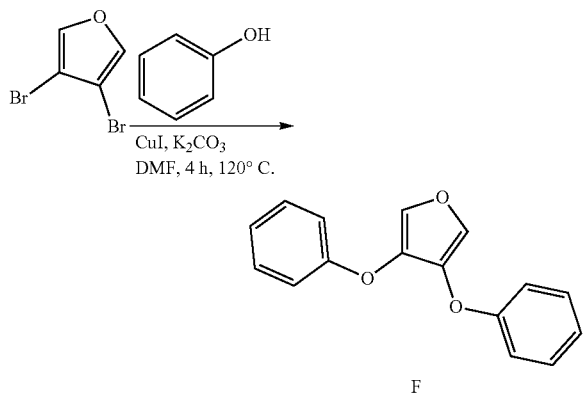

Under an argon (Ar) atmosphere, 300 ml of an anhydrous dichloromethane, 9.881 g of Compound E, 3.4 ml of 2,6-lutidine, and 26.8 g of trityltetrakis(pentafluorophenyl)borate were added to a 500 ml three-necked flask and stirred at room temperature for about 8 hours. After the reaction, solvents were distilled, and the crude product thus obtained was separated by column chromatography (using silica gel) to obtain 4.42 g of Compound 2 as a white solid (yield 45%). The chemical shift values of the compound measured by $^1$H NMR were 7.63-7.57 (3H), 7.51-7.45 (10H), 7.39-7.37 (12H), 7.33-7.28 (4H), 6.94-6.90 (4H). In addition, the molecular weight of Compound 2 measured by FAB-MS was 687. From the results, the white solid compound was identified as Compound 2.

3. Synthesis of Compound 12

(Synthesis of Compound F)

Under an argon (Ar) atmosphere, 18.07 g of 3,4-dibromofuran, 22.59 g of phenol, 3.05 g of CuI and 44.2 g of $K_2CO_3$ were added to a 500 ml, three-necked flask, and stirred in 300 ml of a DMF solvent at about 120° C. for about 4 hours. After cooling in the air, water and toluene were added, an organic layer was separated, and solvents were distilled. The crude product thus obtained was separated by column chromatography (using silica gel) to obtain 14.51 g of Compound F as a white solid (yield 72%). The molecular weight of Compound F measured by FAB-MS was 252.

(Synthesis of Compound 12)

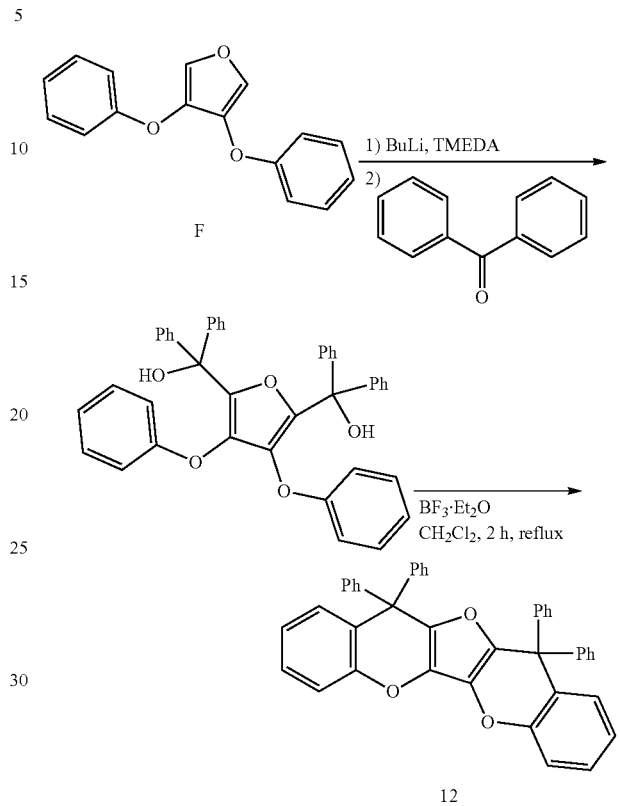

120 ml of an anhydrous THF solution of 9.8 ml of N,N,N',N'-tetramethylethylenediamine (TMEDA) was added to a 500 ml three-necked flask and 36 ml of a hexane solution containing a 1.6 M n-BuLi solution was added thereto dropwisely at about 0° C., followed by stirring for about 2 hours. 7.25 g of Compound F and 60 ml of an anhydrous THF solution were added thereto, followed by stirring at about −78° C. for about 2 hours. 120 ml of an anhydrous THF solution of 10.93 g of benzophenone was added thereto dropwisely, stirred for about 2 hours and stirred at room temperature for about 3 hours. After the reaction, an aqueous solution of 1 N-hydrochloric acid was added thereto and stirred for about 1 hour. The reactant was washed with water. The organic layer thus obtained was concentrated to obtain a viscous material.

The viscous material, 300 ml of anhydrous dichloromethane, and 21.3 ml of $BF_3 \cdot Et_2O$ were added to a 500 ml three-necked flask and under a nitrogen atmosphere, heated and stirred at about 50° C. for about 2 hours for the reaction. After cooling in the air, water was added, an organic layer was separated, and solvents were distilled. The crude product thus obtained was separated by column chromatography (using silica gel) to obtain 11.53 g of Compound 12 as a white solid (yield 69%). The chemical shift values of the compound measured by $^1$H NMR were 7.26 (8H), 7.19-7.17 (6H), 7.10 (8H), 7.02-6.97 (4H), 6.85 (2H). In addition, the molecular weight of Compound 12 measured by FAB-MS was 580. From the results, the white solid compound was identified as Compound 12.

4. Synthesis of Compound 13

(Synthesis of Compound G)

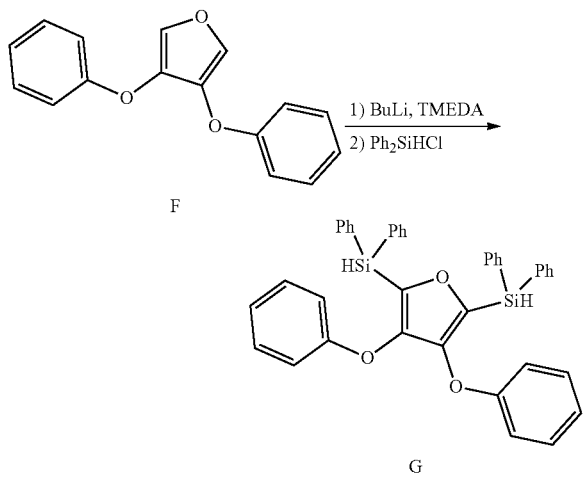

9.8 ml of N,N,N',N'-Tetramethylethylenediamine (TMEDA) and 120 ml of an anhydrous THF solution were added to a 500 ml, three-necked flask, and 36 ml of a hexane solution containing 1.6 M n-BuLi was added thereto at 0° C. dropwisely, followed by stirring for about 2 hours. 60 ml of an anhydrous THF solution of 7.25 g of Compound F was added thereto and stirred at about −78° C. for about 2 hours. 120 ml of an anhydrous THF solution of 11.8 ml of chlorodiphenylsilane was added thereto dropwisely, following by stirring for about 2 hours and stirring at room temperature for about 3 hours. After the reaction, an aqueous solution of 1 N hydrochloric acid was added to the mixture solution and stirred for about 1 hour. The reactant was washed with water, and an organic phase thus obtained was concentrated. The crude product thus obtained was separated by column chromatography (using silica gel) to obtain 14.03 g of Compound G as a white solid (yield 79%). The molecular weight of Compound G measured by FAB-MS was 616.

(Synthesis of Compound 13)

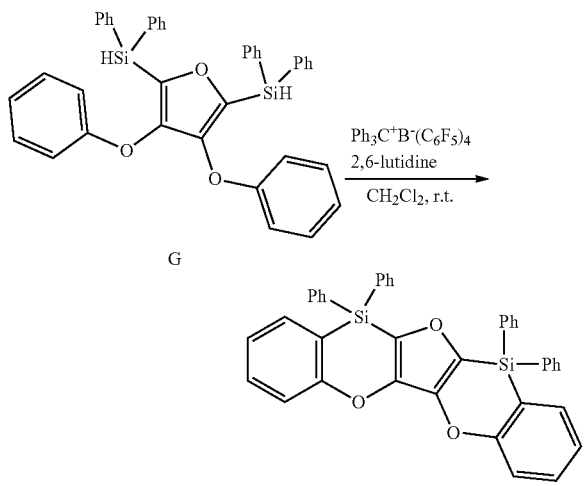

Under an argon (Ar) atmosphere, 250 ml of an anhydrous dichloromethane, 14.0 g of Compound G, 5.6 ml of 2,6-lutidine, and 44.3 g of trityltetrakis(pentafluorophenyl)borate were added to a 500 ml three-necked flask and stirred at room temperature for about 8 hours. After the reaction, solvents were distilled, and the crude product thus obtained was separated by column chromatography (using silica gel) to obtain 5.42 g of Compound 13 as a white solid (yield 39%). The chemical shift values of the compound measured by $^1$H NMR were 7.46 (8H), 7.39-7.37 (12H), 7.33-7.28 (4H), 6.94-6.90 (4H). In addition, the molecular weight of Compound 13 measured by FAB-MS was 612. From the results, the white solid compound was identified as Compound 13.

5. Synthesis of Compound 36

(Synthesis of Compound H)

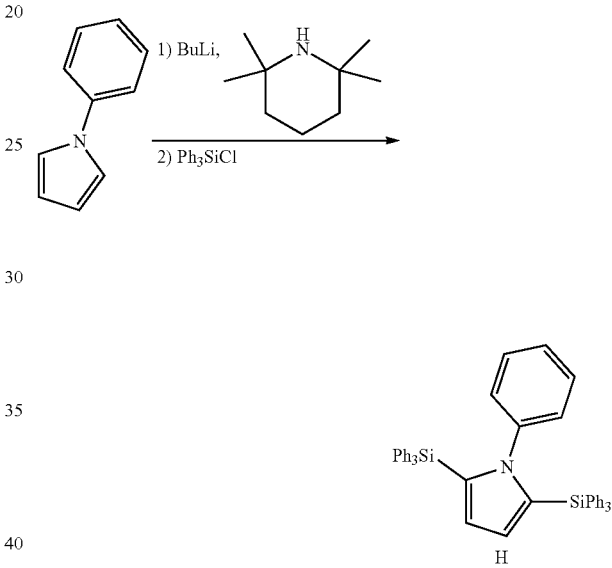

Under an argon (Ar) atmosphere, 80 ml of an anhydrous THF solution of 5.5 ml of 2,2,6,6-tetramethylpiperidine was added to a 500 ml, three-necked flask, and 20 ml of a hexane solution containing 1.6 M n-BuLi was added dropwisely at 0° C., and stirred for about 2 hours. 2.29 g of N-phenylpyrrole and 80 ml of an anhydrous THF solution were added thereto and stirred at about −78° C. for about 2 hours. 9.44 g of chlorotriphenylsilane and 80 ml of an anhydrous THF solution were added thereto dropwisely, following by stirring at about −78° C. for about 2 hours and stirring at room temperature for about 3 hours. After the reaction, an aqueous solution of 1 N hydrochloric acid was added to the mixture solution and stirred for about 1 hour. The reactant was washed with water, and an organic layer thus obtained was concentrated to obtain a viscous material. The crude product thus obtained was separated by column chromatography (using silica gel) to obtain 6.76 g of Compound H as a white solid (yield 64%). The molecular weight of Compound H measured by FAB-MS was 659.

(Synthesis of Compound 1)

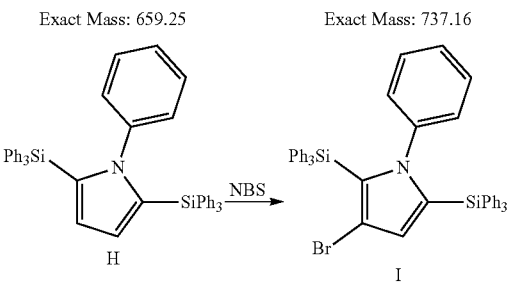

6.75 g of Compound H and 1.83 g of N-bromosuccinimide were added to a 300 ml, round-bottomed flask and stirred in 100 ml of a chloroform solvent at about 0° C. for about 1 hour. After cooling in the air, water was added, an organic layer was separated, and solvents were distilled. The crude product thus obtained was separated by recrystallization using ethanol to obtain 5.95 g of Compound I as a white solid (yield 79%). The molecular weight of Compound I measured by FAB-MS was 737.

(Synthesis of Compound J)

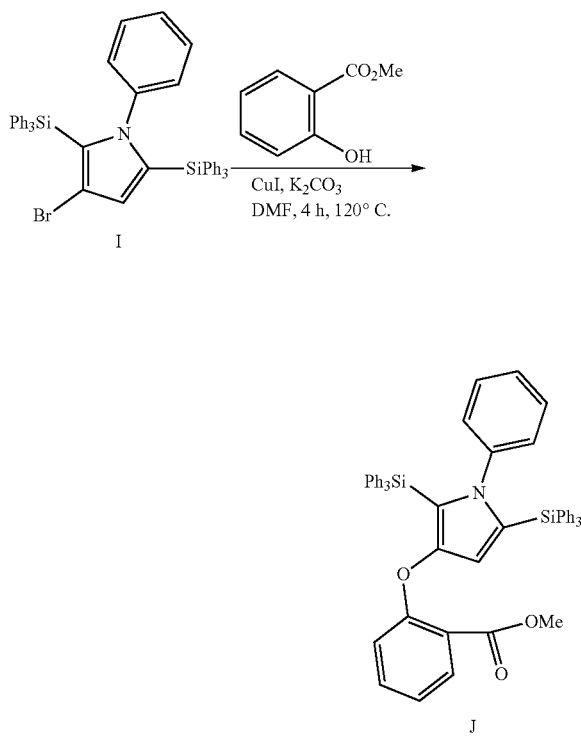

Under an argon (Ar) atmosphere, 5.94 g of Compound I, 1.35 g of methyl salicylate, 0.15 g of CuI and 32.23 g of $K_2CO_3$ were added to a 300 ml, three-necked flask, and stirred in 80 ml of a DMF solvent at about 120° C. for about 4 hours. After cooling in the air, water and toluene were added, an organic layer was separated, and solvents were distilled. The crude product thus obtained was separated by column chromatography (using silica gel) to obtain 5.35 g of Compound J as a white solid (yield 82%). The molecular weight of Compound J measured by FAB-MS was 809.

(Synthesis of Compound 36)

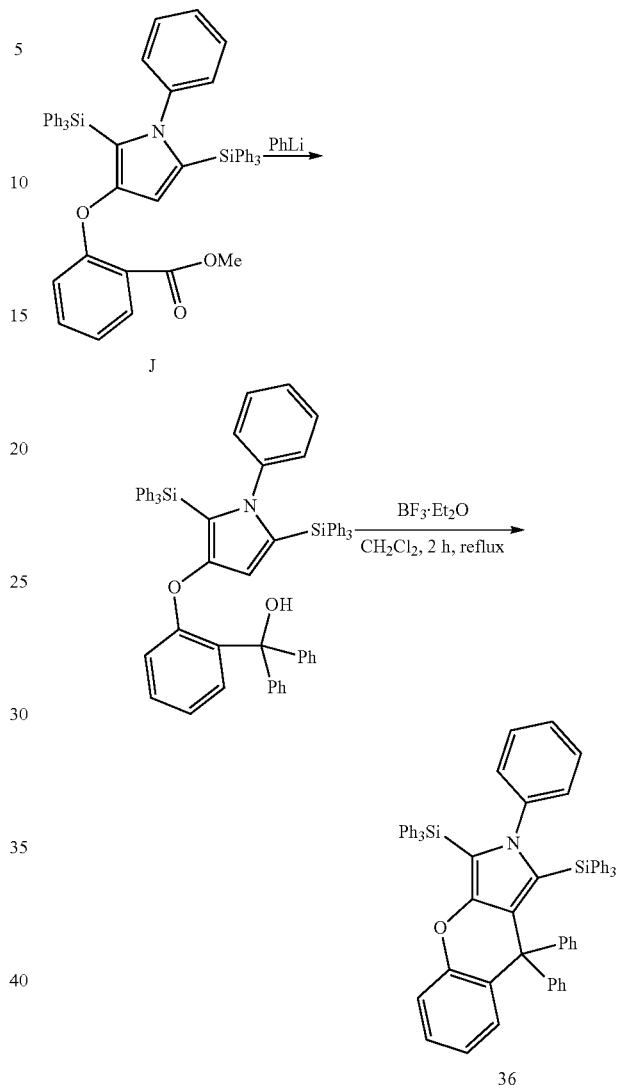

Under an Ar (argon) atmosphere, 1.43 ml of bromobenzene and 30 ml of an anhydrous THF solution were added to a 200 ml three-necked flask and stirred at about −78° C. 8.5 ml of a hexane solution containing 1.6 M n-BuLi was added thereto dropwisely and stirred for about 2 hours. 5.34 g of Compound J and 30 ml of an anhydrous THF solution were added thereto, followed by stirring at about −78° C. for about 2 hours and stirring at room temperature for about 3 hours. After the reaction, an aqueous solution of 1 N-hydrochloric acid was added thereto and stirred for about 1 hour. The reactant was washed with water. The organic layer thus obtained was concentrated to obtain a viscous material.

The viscous material, 70 ml of anhydrous dichloromethane, and 2.5 ml of $BF_3 \cdot Et_2O$ were added to a 200 ml, three-necked flask, and under an argon atmosphere, heated and stirred at about 50° C. for about 2 hours for the reaction. After cooling in the air, water was added, an organic layer was separated, and solvents were distilled. The crude product thus obtained was separated by column chromatography (using silica gel) to obtain 4.29 g of Compound 36 as a white solid (yield 71%). The chemical shift values of the compound measured by ¹H NMR were 7.63-7.57 (3H), 7.51-7.45 (14H), 7.39-7.37 (18H), 7.26 (4H), 7.19-7.17 (3H), 7.10 (4H), 7.02-6.97 (2H), 6.85 (1H). In addition, the molecular weight of Compound 36 measured by FAB-MS was 915. From the results, the white solid compound was identified as Compound 36.

(Examples of Manufacturing Device)

Organic electroluminescence devices of Examples 1 to 5 were manufactured using Compounds 1, 2, 12, 13, and 36 as hole transport materials.

[Example Compounds]

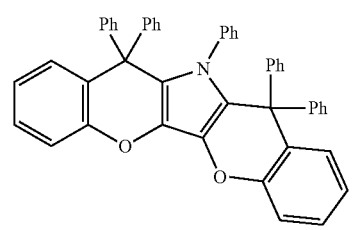

1

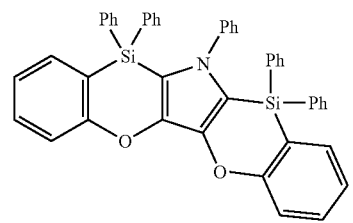

2

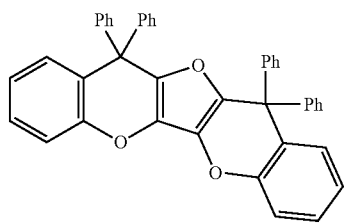

12

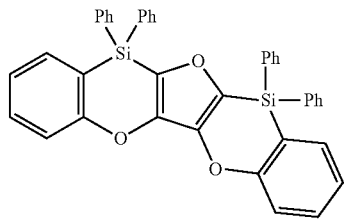

13

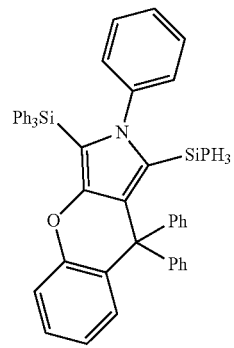

36

Organic electroluminescence devices of Comparative Examples 1 to 5 were manufactured using the following Comparative Compounds c1 to c5 as hole transport materials.

[Comparative Compounds]

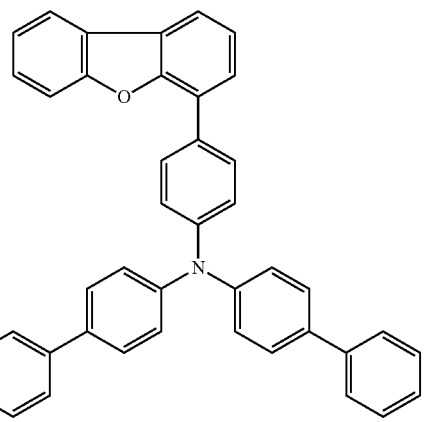

c1

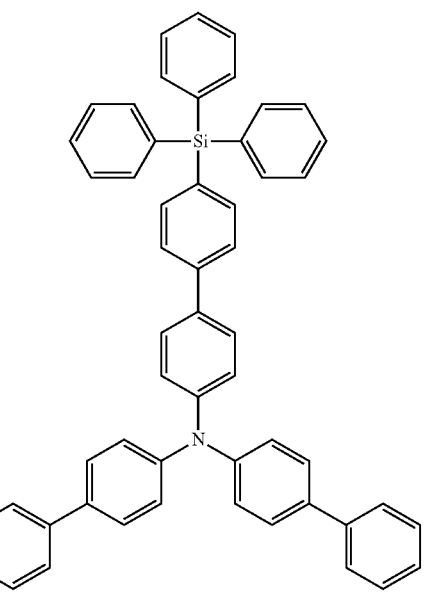

c2

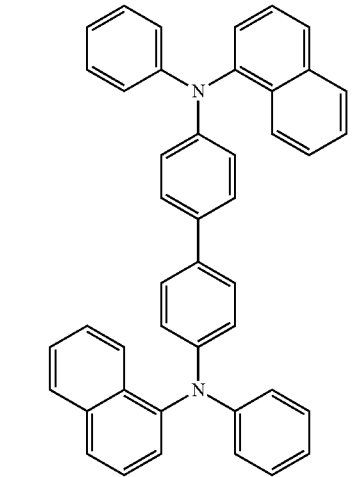

c3

-continued

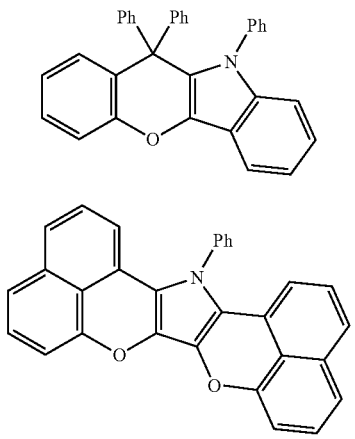
c4 c5

Comparative Compounds c4 and c5 were synthesized as follows.

1. Synthesis of Comparative Compound c4

(Synthesis of Compound K)

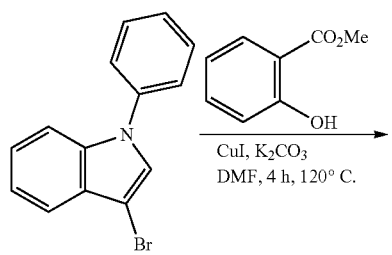

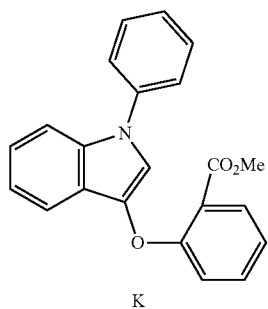
K

Under an argon (Ar) atmosphere, 5.44 g of 3-bromo-N-phenylindole, 2.7 ml of methyl salicylate, 0.38 g of CuI and 35.53 g of $K_2CO_3$ were added to a 300 ml, three-necked flask, and stirred in 80 ml of a DMF solvent at about 120° C. for about 4 hours. After cooling in the air, water and toluene were added, an organic layer was separated, and solvents were distilled. The crude product thus obtained was separated by column chromatography (using silica gel) to obtain 5.29 g of Compound K as a white solid (yield 77%). The molecular weight of Compound K measured by FAB-MS was 343.

(Synthesis of Comparative Compound c4)

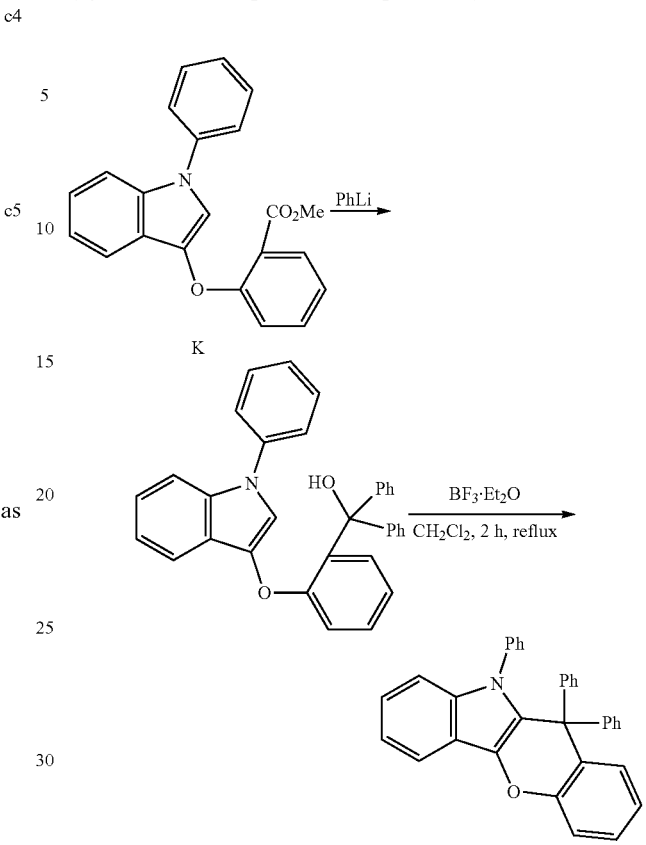
c4

Under an argon (Ar) atmosphere, 3.3 ml of bromobenzene and 160 ml of an anhydrous THF solution were added to a 500 ml three-necked flask and stirred at about −78° C. 19.5 ml of a hexane solution containing 1.6 M n-BuLi was added thereto dropwisely and stirred for about 2 hours. 80 ml of an anhydrous THF solution of 5.28 g of Compound K was added thereto, followed by stirring at about −78° C. for about 2 hours and stirring at room temperature for about 3 hours. After the reaction, an aqueous solution of 1 N-hydrochloric acid was added thereto and stirred for about 1 hour. The reactant was washed with water. The organic layer thus obtained was concentrated to obtain a viscous material.

The viscous material, 160 ml of anhydrous dichloromethane, and 5.8 ml of $BF_3 \cdot Et_2O$ were added to a 300 ml, three-necked flask, and under an argon atmosphere, heated and stirred at about 50° C. for about 2 hours for the reaction. After cooling in the air, water was added, an organic layer was separated, and solvents were distilled. The crude product thus obtained was separated by column chromatography (using silica gel) to obtain 3.88 g of Compound c4 as a white solid (yield 56%). The chemical shift values of the compound measured by $^1H$ NMR were 7.99-7.93 (2H), 7.67-7.49 (5H), 7.36-7.09 (12H), 7.02-6.97 (3H), 6.85 (1H). In addition, the molecular weight of Compound c4 measured by FAB-MS was 449. From the results, the white solid compound was identified as Compound c4.

2. Synthesis of Comparative Compound c5

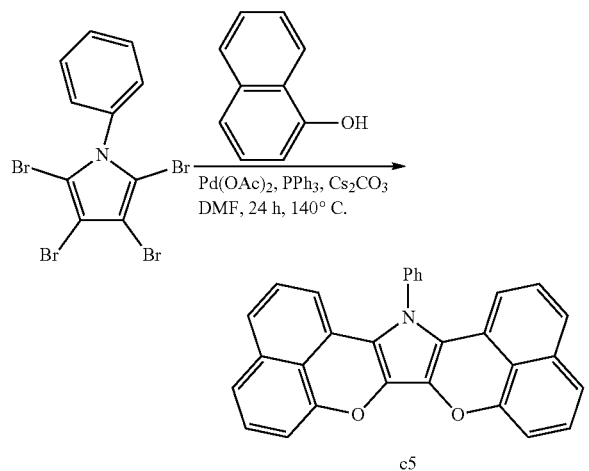

Under an argon (Ar) atmosphere, 13.8 g of 2,3,4,5-tetrabromo-N-phenylpyrrole, 8.65 g of 1-naphthol, 20.40 g of $Pd(OAc)_3$, 31.89 g of $PPh_3$, and 358.6 g of $Cs_2CO_3$ were added to a 300 ml, three-necked flask and stirred in 120 ml of a DMF solvent at about 120° C. for about 4 hours. After cooling in the air, water and toluene were added, an organic layer was separated, and solvents were distilled. The crude product thus obtained was separated by column chromatography (using silica gel) to obtain 3.68 g of Compound c5 as a white solid (yield 29%). The chemical shift values of the compound measured by $^1$H NMR were 8.20 (2H), 8.09 (2H), 7.97 (2H), 7.73 (2H), 7.63-7.57 (3H), 7.50 (2H), 7.43 (2H), 6.28 (2H). In addition, the molecular weight of Compound c5 measured by FAB-MS was 423. From the results, the white solid compound was identified as Compound c5.

(Manufacture of Organic Electroluminescence Device)

Organic electroluminescence devices of Examples 1 to 3 and Comparative Examples 1 to 5 were manufactured by forming a first electrode using ITO to a thickness of about 150 nm, a hole injection layer using hexaazatriphenylene-hexacarbonitrile (HAT-CN) to a thickness of about 10 nm, a first hole transport layer using NPB to a thickness of about 40 nm, second hole transport layers using the compounds of the Examples and the Comparative Examples to a thickness of about 10 nm, an emission layer using 1,3-bis(N-carbazolyl)benzene (mCP) doped with 8% bis[2-(4,6-difluorophenyl)pyridinato-C2,N](picolinato)iridium(III) (FIrpic) to a thickness of about 20 nm, an electron transport layer using 1,3,5-tris(1-phenyl-1H-benzimidazol-2-yl)benzene (TPBi) to a thickness of about 40 nm, an electron injection layer using Liq to a thickness of about 2 nm, and a second electrode using Al to a thickness of about 120 nm. Each layer and the second electrode were formed by a vacuum deposition method.

Then, the emission efficiency of the organic electroluminescence devices was evaluated. The emission efficiency was relative emission efficiency ratio of each of the Examples and Comparative Examples when the emission efficiency of the organic electroluminescence device of Comparative Example 1 was 100%.

The emission efficiency of the device was measured in a dark room using a Source Meter of 2400 Series of Keithley Instruments, a color brightness photometer CS-200 of Konica Minolta Holdings Co., Ltd, PC Program LabVIEW 8.2 for measurement of National Instruments Japan.

TABLE 1

| Device manufacturing example | Second hole transport layer | Emission efficiency (relative ratio with respect to Comparative Example 1) |
| --- | --- | --- |
| Example 1 | Example Compound 1 | 130% |
| Example 2 | Example Compound 2 | 125% |
| Example 3 | Example Compound 12 | 115% |
| Example 4 | Example Compound 13 | 125% |
| Example 5 | Example Compound 36 | 125% |
| Comparative Example 1 | Comparative Compound c1 | 100% |
| Comparative Example 2 | Comparative Compound c2 | 95% |
| Comparative Example 3 | Comparative Compound c3 | 90% |
| Comparative Example 4 | Comparative Compound c4 | 100% |
| Comparative Example 5 | Comparative Compound c5 | 80% |

From the results in Table 1, it may be found that the organic electroluminescence device including the polycyclic compound according to an embodiment may attain high emission efficiency.

When comparing Examples 1 to 5 and Comparative Examples 1 to 5, the organic electroluminescence device including the polycyclic compound according to an embodiment attained high emission efficiency. Without being bound by theory, it is believed that this is because the compound corresponding to Formula 1 has hole transport properties and a high triplet energy level and is disposed in a hole transport layer adjacent to an emission layer, thereby suppressing the diffusion of triplet excitons generated in the emission layer toward a hole transport region.

In Comparative Examples 1 to 3, the compound applied in the hole transport layer does not have a five-membered heteroaryl group as a base skeleton but instead has a directly connected structure of amine with a benzene ring. The triplet energy level and emission efficiency of the comparative compounds were lower than those of the compounds of Examples 1 to 5.

Comparative Compound c4 of Comparative Example 4 is a polycyclic compound having pyrrole as a base skeleton, but an aromatic hydrocarbon ring is directly condensed with pyrrole which is a heteroaryl group. The triplet energy level is lower than the compounds of the examples, and emission efficiency was decreased.

Comparative Compound c5 of Comparative Example 5 has pyrrole which is a heteroaryl group as a base skeleton, but benzene rings are condensed with a benzene ring at both sides thereof to form a naphthalene shape. The triple energy level is lower than the compounds of the Examples, and emission efficiency was decreased.

As described above, embodiments may provide a polycyclic compound for an organic electroluminescence device having high emission efficiency. Embodiments may also provide an organic electroluminescence device having high emission efficiency.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A polycyclic compound represented by the following Formula 1:

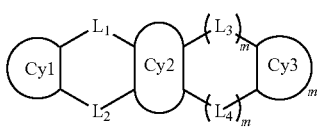

[Formula 1]

where $L_1$ to $L_4$ are each independently a substituted or unsubstituted divalent alkyl group having 1 to 10 carbon atoms, a substituted or unsubstituted divalent amino group, a substituted or unsubstituted divalent oxy group, a substituted or unsubstituted divalent thio group, a substituted or unsubstituted divalent sulfoxy group, a substituted or unsubstituted divalent phosphine oxide group, or a substituted or unsubstituted divalent silyl group, m is 0 or 1, and Cy1 to Cy3 are each independently represented by the following Formula 2-1 or 2-2, where one of Cy1 or Cy2 is represented by the following Formula 2-2:

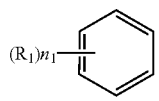

[Formula 2-1]

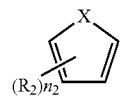

[Formula 2-2]

where X is one of O, S, or $NY_1$, $R_1$ and $R_2$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted oxy group, a substituted or unsubstituted thio group, a substituted or unsubstituted boron group, a substituted or unsubstituted sulfoxy group, a substituted or unsubstituted phosphine oxide group, a substituted or unsubstituted carbonyl group, a substituted or unsubstituted amino group, or a substituted or unsubstituted silyl group, $Y_1$ is a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted boron group, a substituted or unsubstituted sulfoxy group, a substituted or unsubstituted phosphine oxide group, a substituted or unsubstituted carbonyl group, or a substituted or unsubstituted silyl group, $n_1$ is an integer of 0 to 4, and $n_2$ is an integer of 0 to 2, 1) wherein when m is 1, $n_2$ is 0, one of $L_1$ and $L_2$ is a substituted divalent amino group, one of $L_3$ and $L_4$ is a substituted divalent amino group, Cy2 is represented by Formula 2-2, and Cy1 and Cy3 are each represented by Formula 2-1, an other one of $L_1$ and $L_2$ and/or an other one of $L_3$ and $L_4$ is a substituted or unsubstituted divalent amino group, a substituted or unsubstituted divalent oxy group, a substituted or unsubstituted divalent thio group, a substituted or unsubstituted divalent sulfoxy group, a substituted or unsubstituted divalent phosphine oxide group, or a substituted or unsubstituted divalent silbyl group, 2) wherein when m is 0, i) at least one selected from $L_1$ and $L_2$ is a divalent methyl group substituted with an unsubstituted phenyl group, or a divalent silyl group substituted with a phenyl group, ii) when one of $L_1$ and $L_2$ is the divalent methyl group, and when an other one of $L_1$ and $L_2$ is $NY_1$, $Y_1$ does not join with an adjacent group to form a ring, iii) when $L_1$ and $L_2$ are each a divalent methyl group, $L_1$ and $L_2$ are each substituted with two unsubstituted phenyl groups, and iv) when one of $L_1$ and $L_2$ is a divalent methyl group and an other one of $L_1$ and $L_2$ is a divalent silyl group, the divalent methyl group and the divalent silyl group are each substituted with two unsubstituted phenyl groups, 3) wherein when m is O and Cy1 and Cy2 are each represented by Formula 2-2, i) X of Cy1 or Cy2 is O or $NY_1$, and ii) when one of $L_1$ and $L_2$ is a divalent methyl group and an other one of $L_1$ and $L_2$ is a substituted or unsubstituted divalent amino group, the divalent methyl group is substituted with two unsubstituted phenyl groups, 4) wherein when m is 1, $n_1$ is 1, one of $L_1$ and $L_2$ is a divalent thio group, one of $L_3$ and $L_4$ is a divalent thio group, Cy2 is represented by Formula 2-2, $n_2$ is O, X is S, and Cy1 and Cy3 are each represented by Formula 2-1, another one of $L_1$ and $L_2$ and/or another one of $L_3$ and $L_4$ is a divalent alkyl group having 1 to 10 carbon atoms and substituted with a substituted or unsubstituted aryl group having 6 to 15 carbon atoms for forming a ring, a divalent amino group substituted with a substituted or unsubstituted aryl group having 6 to 15 carbon atoms for forming a ring, or a divalent silyl group substituted with a substituted or unsubstituted aryl group having 6 to 15 carbon atoms for forming a ring, and 5) wherein when m is 1, Cy1 and Cy3 are each independently represented by the Formula 2-2, Cy2 is represented by Formula 2-1, X is $NY_1$, and $L_1$ to $L_4$ are each a substituted divalent methyl group, the substituted divalent methyl group is a methyl group substituted with two unsubstituted phenyl groups.

2. The polycyclic compound as claimed in claim 1, wherein the polycyclic compound represented by Formula 1 is represented by one of the following Formulae 3-1 to 3-4:

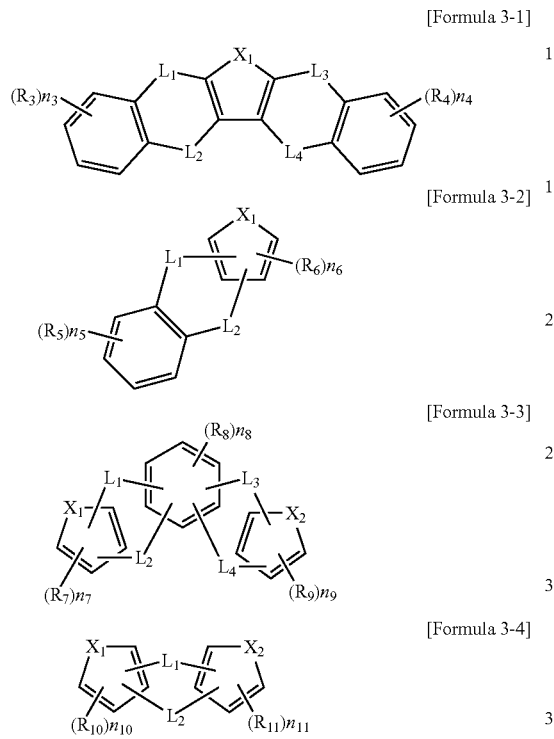

[Formula 3-1]

[Formula 3-2]

[Formula 3-3]

[Formula 3-4]

where $X_1$ and $X_2$ are each independently one of O, S, or $NY_1$, $R_3$ to $R_{11}$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted oxy group, a substituted or unsubstituted thio group, a substituted or unsubstituted boron group, a substituted or unsubstituted sulfoxy group, a substituted or unsubstituted phosphine oxide group, a substituted or unsubstituted carbonyl group, a substituted or unsubstituted amino group, or a substituted or unsubstituted silyl group, $n_3$ to $n_5$ are each independently an integer of 0 to 4, $n_6$ to $n_{11}$ are each independently an integer of 0 to 2, and $Y_1$ and $L_1$ to $L_4$ are the same as defined in claim 1, and wherein in Formula 3-4, when one of L1 and L2 is a divalent methyl group and an other one of L1 and L2 is a substituted or unsubstituted divalent amino group, the divalent methyl group is substituted with two unsubstituted phenyl groups.

3. The polycyclic compound as claimed in claim 2, wherein the polycyclic compound represented by Formula 3-2 is represented by following Formula 3-2-1 or 3-2-2:

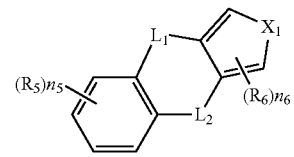

[Formula 3-2-1]

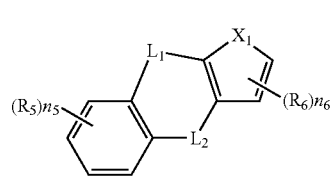

[Fomrula 3-2-2]

where $L_1$, $L_2$, $R_5$, $R_6$, $X_1$, $n_5$ and $n_6$ are the same as defined in claim 2.

4. The polycyclic compound as claimed in claim 2, wherein the polycyclic compound represented by Formula 3-3 is represented by the following Formula 3-3-1 or 3-3-2:

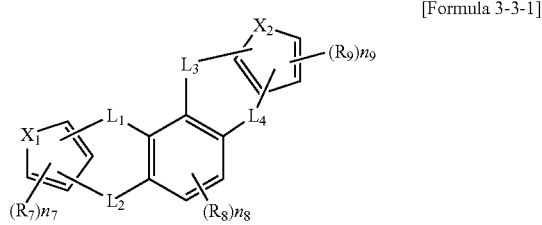

[Formula 3-3-1]

[Formula 3-3-2]

where $L_1$, $L_2$, $L_3$, $L_4$, $R_7$, $R_8$, $R_9$, $X_1$, $X_2$, $n_7$, $n_8$ and $n_9$ are the same as defined in claim 2.

5. The polycyclic compound as claimed in claim 2, wherein the polycyclic compound represented by Formula 3-4 is represented by the following Formula 3-4-1 or 3-4-2:

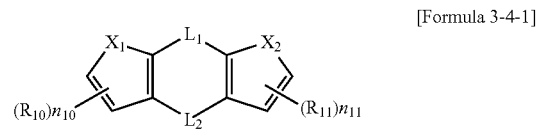

[Formula 3-4-1]

[Formula 3-4-2]

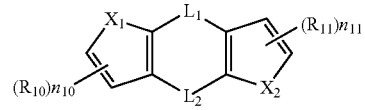

where $L_1$, $L_2$, $R_{10}$, $R_{11}$, $X_1$, $X_2$, $n_{10}$ and $n_{11}$ are the same as defined in connection with Formula 3-4.

6. The polycyclic compound as claimed in claim 1, wherein $L_1$ to $L_4$ are each independently a substituted or unsubstituted divalent alkyl group having 1 to 10 carbon atoms, a substituted or unsubstituted divalent silyl group, a substituted or unsubstituted divalent oxy group, or a substituted or unsubstituted divalent thio group.

7. The polycyclic compound as claimed in claim 1, wherein $L_1$ to $L_4$ are each independently a divalent alkyl group having 1 to 10 carbon atoms and substituted with a substituted or unsubstituted aryl group having 6 to 15 carbon atoms for forming a ring, a divalent amino group substituted with a substituted or unsubstituted aryl group having 6 to 15 carbon atoms for forming a ring, or a divalent silyl group substituted with a substituted or unsubstituted aryl group having 6 to 15 carbon atoms for forming a ring.

8. The polycyclic compound as claimed in claim 1, wherein $R_1$ and $R_2$ are each independently a substituted or unsubstituted aryl group having 6 to 15 carbon atoms for forming a ring, or the substituted or unsubstituted silyl group.

9. The polycyclic compound as claimed in claim 1, wherein the polycyclic compound represented by Formula 1 is one of compounds represented in the following Compound Group 1:

[Compound Group 1]

1
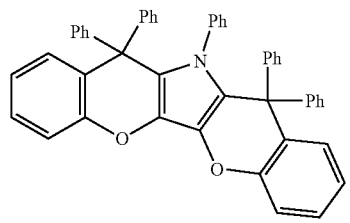

2
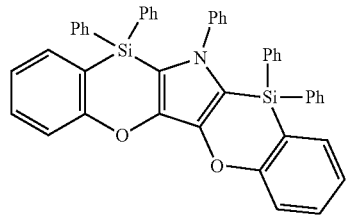

3
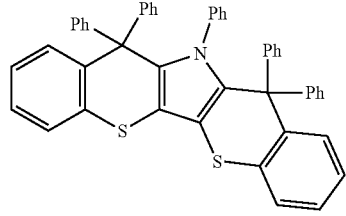

4
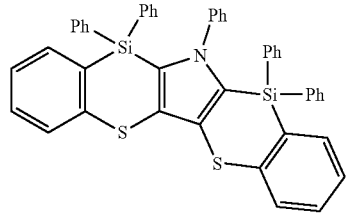

5
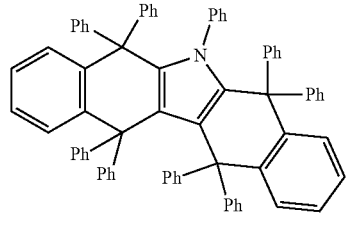

6
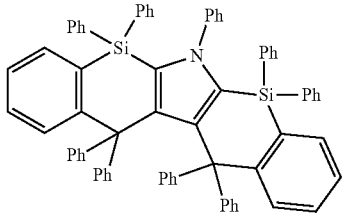

7
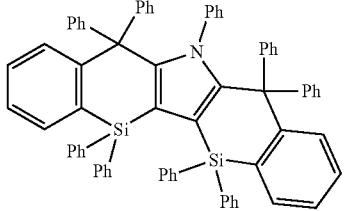

8
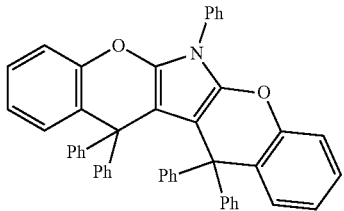

9
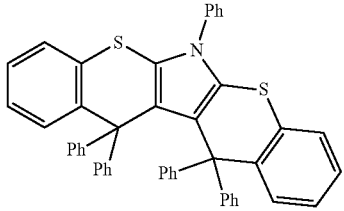

10
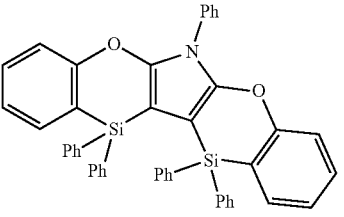

11
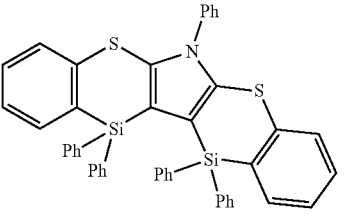

12
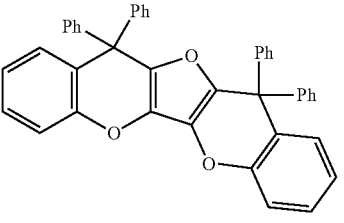

13
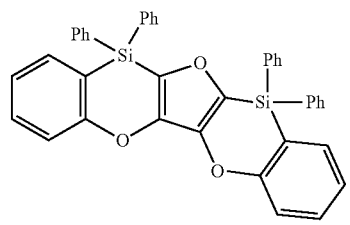
14
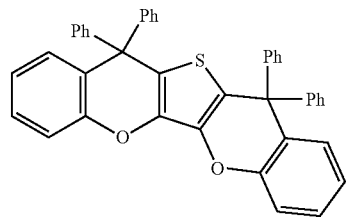
15
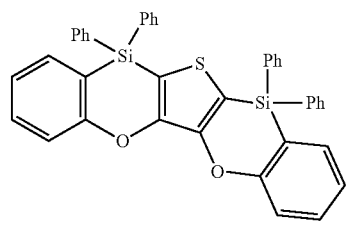
17
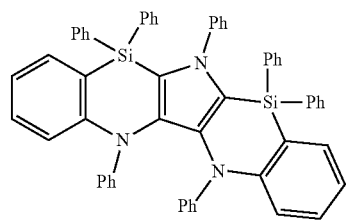
19
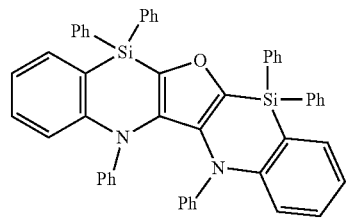
20
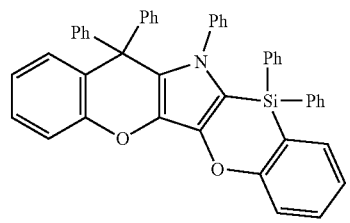
21
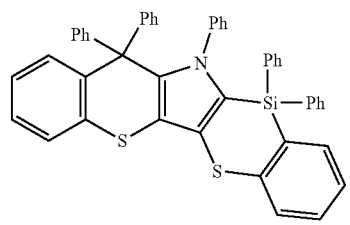
22
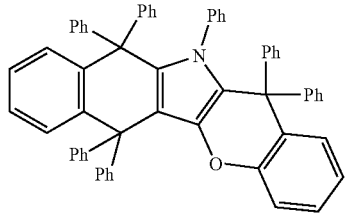
23
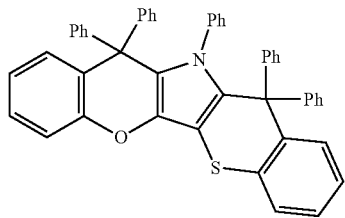
24
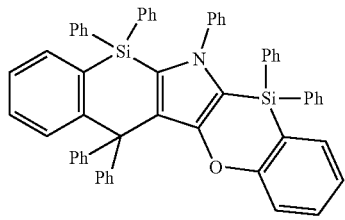
25
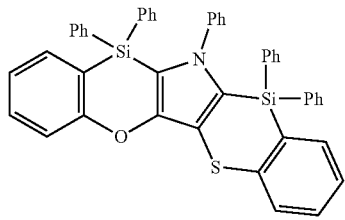
26
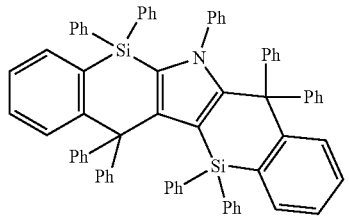
27
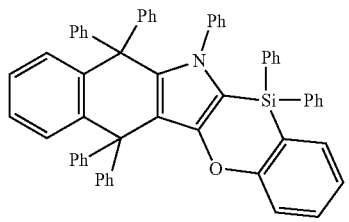
28
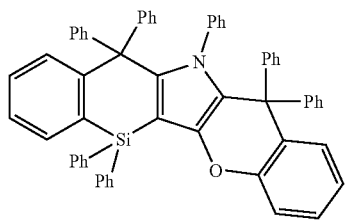

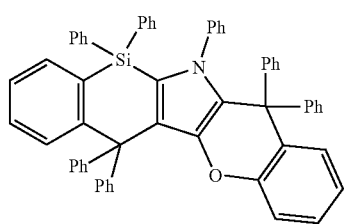
29
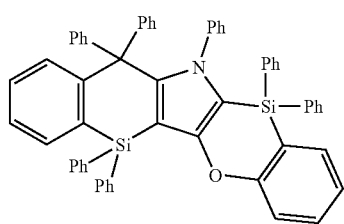
30
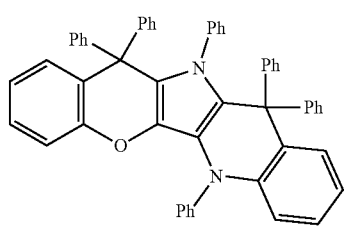
31
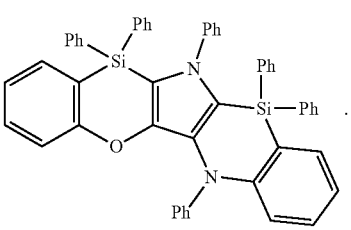
32
10. The polycyclic compound as claimed in claim 1, wherein the polycyclic compound represented by Formula 1 is one selected from compounds represented in the following Compound Group 2:
[Compound Group 2]
33
34
35
36
37

38
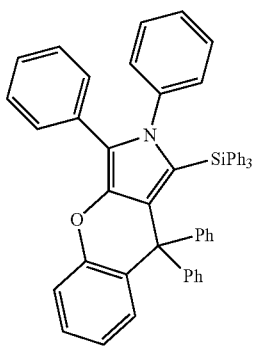
39
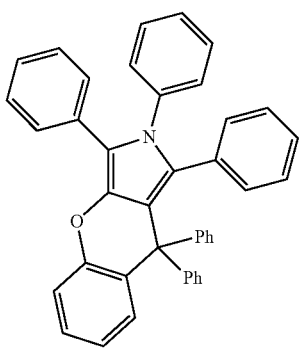
40
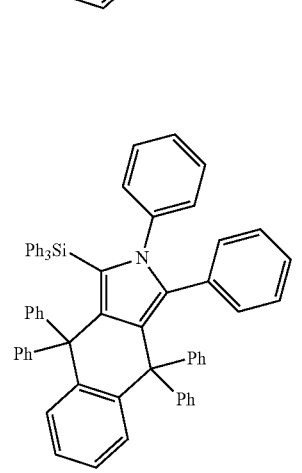
41
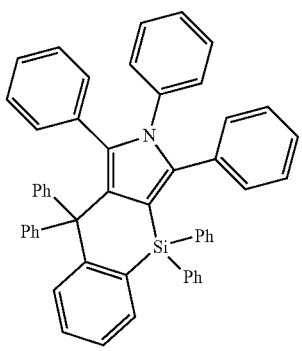
42
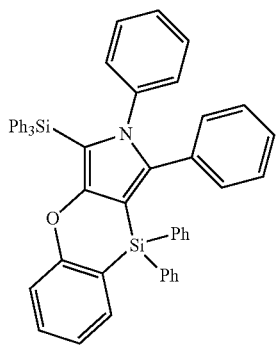
43
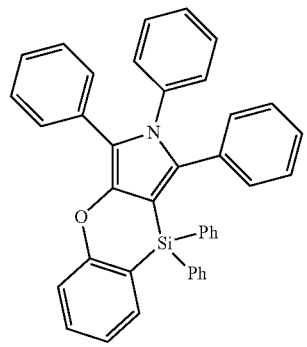
44
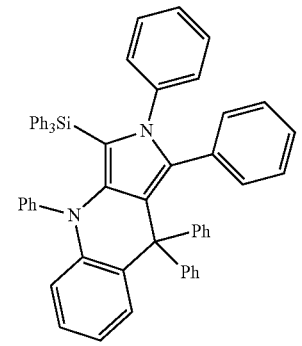
45
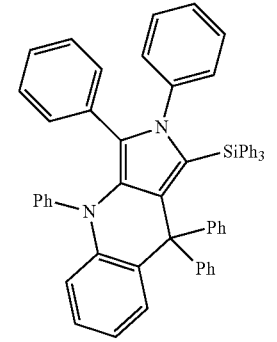

46
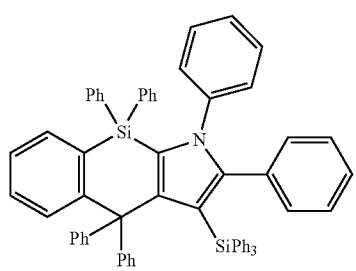
47
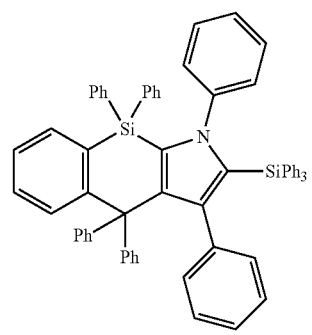
48
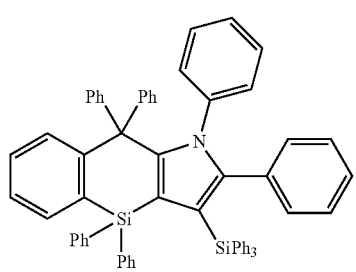
49
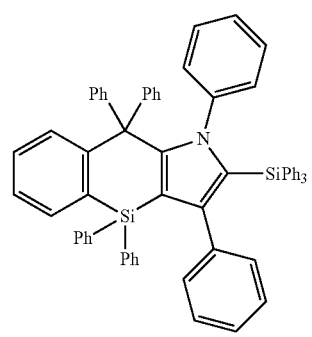
50
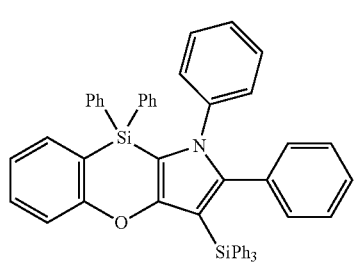
51
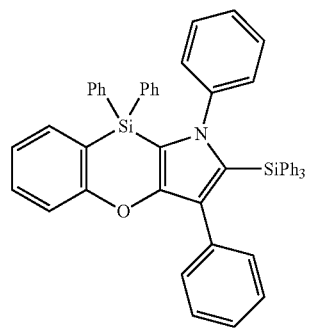
52
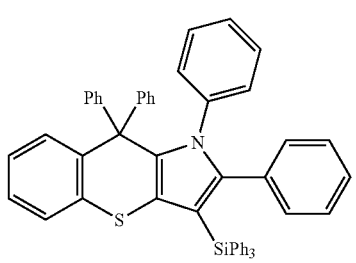
53
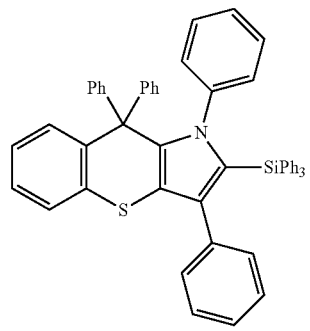
54
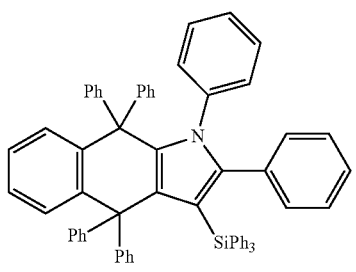
55
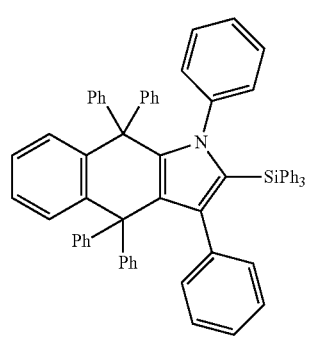

-continued
56
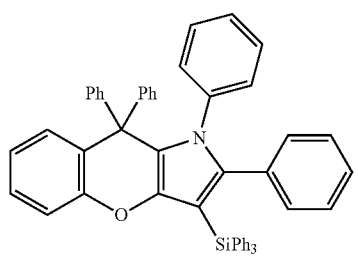
57
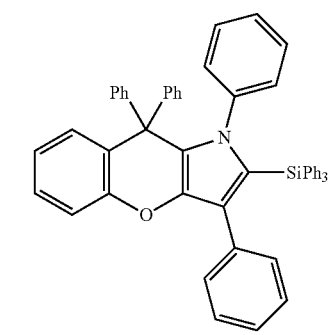
58
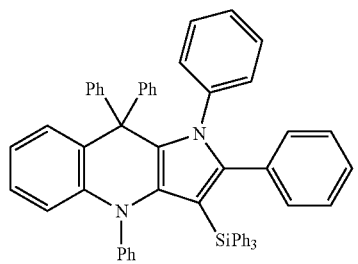
59
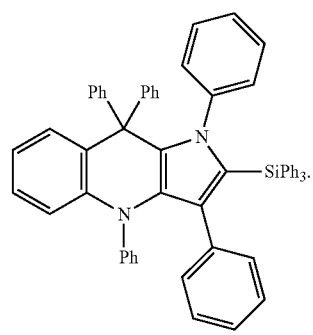
11. The polycyclic compound as claimed in claim 1, wherein the polycyclic compound represented by Formula 1 is one selected from compounds represented in the following Compound Group 3:
[Compound Group 3]
60
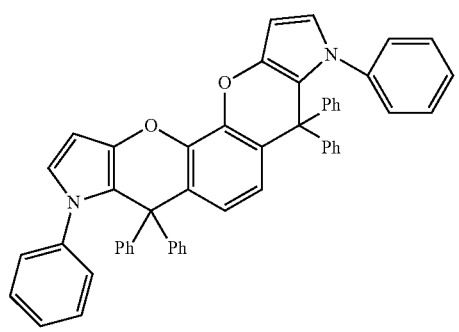
61
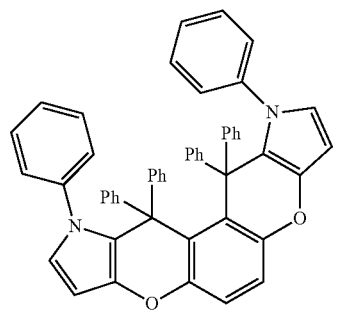
62
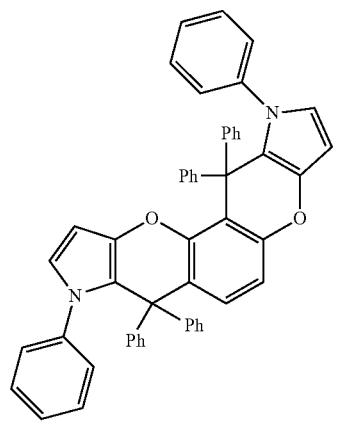
63
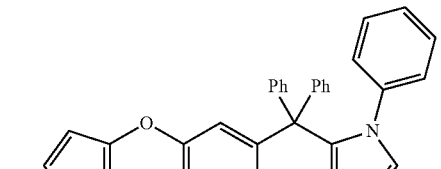
64
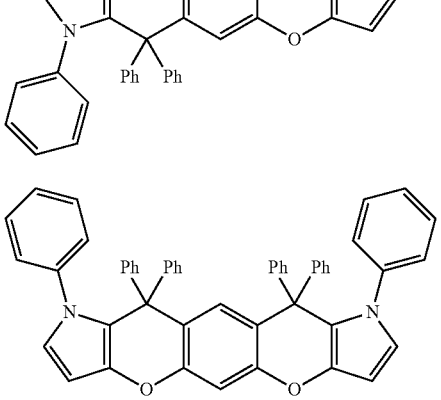

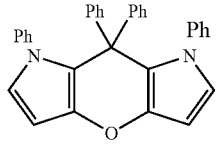

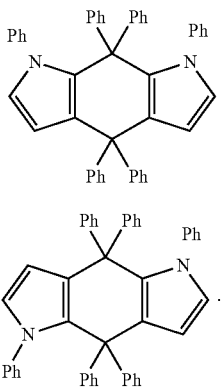

12. An organic electroluminescence device, comprising:
a first electrode;
a hole transport region provided on the first electrode;
an emission layer provided on the hole transport region;
an electron transport region provided on the emission layer; and
a second electrode provided on the electron transport region,
wherein the hole transport region comprises a polycyclic compound represented by the following Formula 1:

[Formula 1]

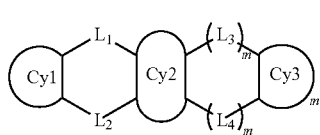

where $L_1$ to $L_4$ are each independently a substituted or unsubstituted divalent alkyl group having 1 to 10 carbon atoms, a substituted or unsubstituted divalent amino group, a substituted or unsubstituted divalent oxy group, a substituted or unsubstituted divalent thio group, a substituted or unsubstituted divalent sulfoxy group, a substituted or unsubstituted divalent phosphine oxide group, or a substituted or unsubstituted divalent silyl group, m is 0 or 1, and Cy1 to Cy3 are each independently represented by the following Formula 2-1 or 2-2, where one of Cy1 or Cy2 is represented by the following Formula 2-2:

[Formula 2-1]

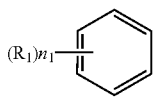

[Formula 2-2]

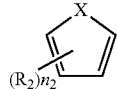

where X is one of O, S, or $NY_1$, $R_1$ and $R_2$ are each independently a hydrogen atom, a deuterium atom, a halogen atom, a substituted or unsubstituted alkyl group having 1 to 10 carbon atoms, a substituted or unsubstituted aryl group having 6 to 30 carbon atoms, a substituted or unsubstituted heteroaryl group having 2 to 30 carbon atoms for forming a ring, a substituted or unsubstituted oxy group, a substituted or unsubstituted thio group, a substituted or unsubstituted boron group, a substituted or unsubstituted sulfoxy group, a substituted or unsubstituted phosphine oxide group, a substituted or unsubstituted carbonyl group, a substituted or unsubstituted amino group, or a substituted or unsubstituted silyl group, $Y_1$ is a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted boron group, a substituted or unsubstituted sulfoxy group, a substituted or unsubstituted phosphine oxide group, a substituted or unsubstituted carbonyl group, or a substituted or unsubstituted silyl group, $n_1$ is an integer of 0 to 4, and $n_2$ is an integer of 0 to 2, wherein when m is 1, $n_2$ is 0, one of $L_1$ and $L_2$ is a substituted divalent amino group, one of $L_3$ and $L_4$ is a substituted divalent amino group, Cy2 is represented by Formula 2-2, and Cy1 and Cy3 are each represented by Formula 2-1, an other one of $L_1$ and $L_2$ and/or an other one of $L_3$ and $L_4$ is a substituted or unsubstituted divalent amino group, a substituted or unsubstituted divalent oxy group, a substituted or unsubstituted divalent thio group, a substituted or unsubstituted divalent sulfoxy group, a substituted or unsubstituted divalent phosphine oxide group, or a substituted or unsubstituted divalent silyl group, and wherein when m is 0, i) at least one selected from $L_1$ and $L_2$ is a divalent methyl group substituted with an unsubstituted phenyl group, or a divalent silyl group substituted with a phenyl group, and ii) when one of $L_1$ and $L_2$ is the divalent methyl group, and when an other one of $L_1$ and $L_2$ is $NY_1$, $Y_1$ does not join with an adjacent group to form a ring, wherein when m is 0 and Cy1 and Cy2 are each represented by Formula 2-2, X of Cy1 or Cy2 is O or $NY_1$, and wherein when m is 1, $n_1$ is 1, one of $L_1$ and $L_2$ is a divalent thio group, one of $L_3$ and $L_4$ is a divalent thio group, Cy2 is represented by Formula -2, $n_2$ is 0, X is S, and Cy1 and Cy3 are each represented by Formula 2-1, an other one of $L_1$ and $L_2$ and/or an other one of $L_3$ and $L_4$ is a divalent alkyl group having 1 to 10 carbon atoms and substituted with a substituted or unsubstituted aryl group having 6 to 15 carbon atoms for forming a ring, a divalent amino group substituted with a substituted or unsubstituted aryl group having 6 to 15 carbon atoms for forming a ring, or a divalent silyl group substituted with a substituted or unsubstituted aryl group having 6 to 15 carbon atoms for forming a ring.

13. The organic electroluminescence device as claimed in claim 12, wherein the hole transport region includes:
a hole injection layer disposed on the first electrode; and
a hole transport layer disposed on the hole injection layer,
wherein the hole transport layer comprises the polycyclic compound represented by Formula 1.

14. The organic electroluminescence device as claimed in claim 12, wherein the hole transport region includes:
a hole injection layer disposed on the first electrode;
a first hole transport layer disposed on the hole injection layer; and
a second hole transport layer disposed on the first hole transport layer and adjacent to the emission layer,
wherein the second hole transport layer includes the polycyclic compound represented by Formula 1.

15. The organic electroluminescence device as claimed in claim 12, wherein the polycyclic compound represented by Formula 1 is represented by one of the following Formulae 3-1 to 3-4:

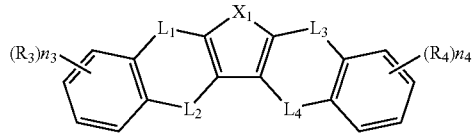

[Formula 3-1]

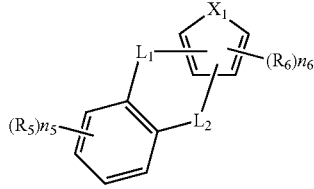

[Formula 3-2]

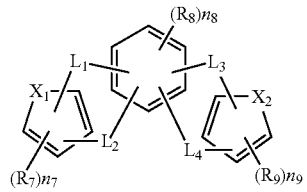

[Formula 3-3]

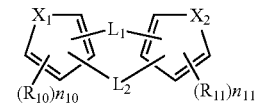

[Formula 3-4]

where $X_1$ and $X_2$ are each independently one of O, S, or $NY_1$, and in Formula 3-4, $X_1$ and/or $X_2$ is O or $NY_1$,
$R_3$ to $R_{11}$ are each independently a deuterium atom, a halogen atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted oxy group, a substituted or unsubstituted thio group, a substituted or unsubstituted boron group, a substituted or unsubstituted sulfoxy group, a substituted or unsubstituted phosphine oxide group, a substituted or unsubstituted carbonyl group, a substituted or unsubstituted amino group, or a substituted or unsubstituted silyl group,
$n_3$ to $n_5$ are an integer of 0 to 4,
$n_6$ to $n_{11}$ are an integer of 0 to 2, and
$Y_1$ and $L_1$ to $L_4$ are the same as defined in claim 12.

16. The organic electroluminescence device as claimed in claim 15, wherein the polycyclic compound represented by Formula 3-2 is represented by the following Formula 3-2-1 or 3-2-2:

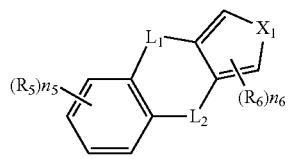

[Formula 3-2-1]

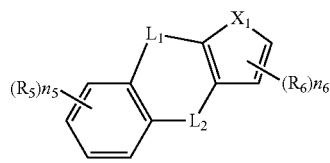

[Formula 3-2-2]

where $L_1$, $L_2$, $R_5$, $R_6$, $X_1$, $n_5$ and $n_6$ are the same as defined in claim 15.

17. The organic electroluminescence device as claimed in claim 15, wherein the polycyclic compound represented by Formula 3-3 is represented by the following Formula 3-3-1 or 3-3-2:

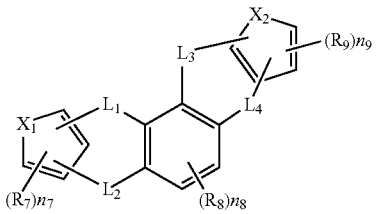

[Formula 3-3-1]

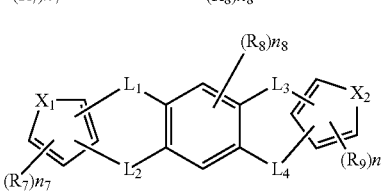

[Formula 3-3-2]

where $L_1$, $L_2$, $L_3$, $L_4$, $R_7$, $R_8$, $R_9$, $X_1$, $X_2$, $n_7$, $n_8$ and $n_9$ are the same as defined in claim 15.

18. The organic electroluminescence device as claimed in claim 15, wherein the polycyclic compound represented by Formula 3-4 is represented by the following Formula 3-4-1 or 3-4-2:

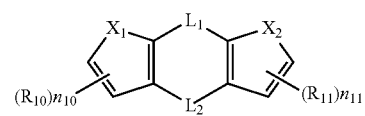

[Formula 3-4-1]

[Formula 3-4-2]
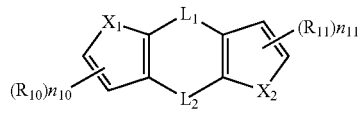
where $L_1$, $L_2$, $R_{10}$, $R_{11}$, $X_1$, $X_2$, $n_{10}$ and $n_{11}$ are the same as defined in connection with Formula 3-4.
19. The organic electroluminescence device as claimed in claim 12, wherein the polycyclic compound represented by Formula 1 is one selected from compounds represented in the following Compound Groups 1 to 3:
[Compound Group 1]
1
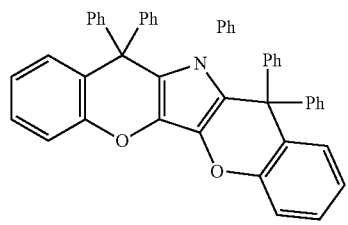
2
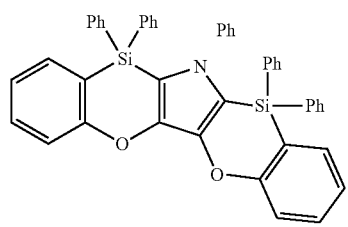
3
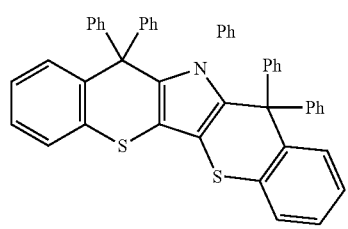
4
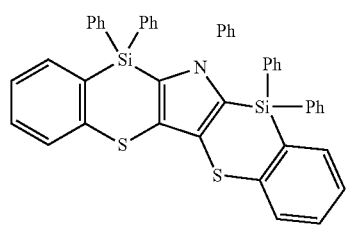
5
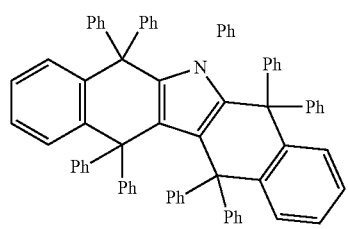
6
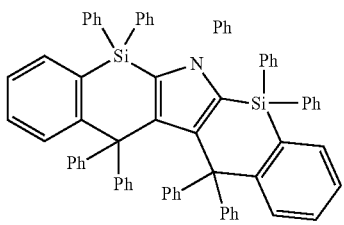
7
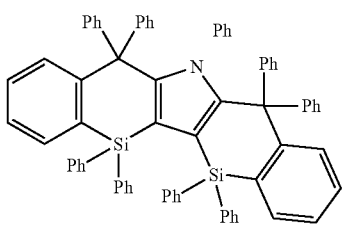
8
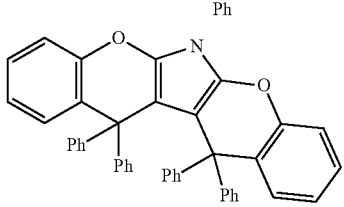
9
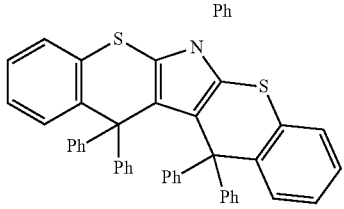
10
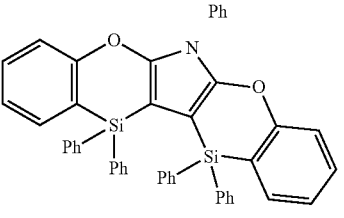
11
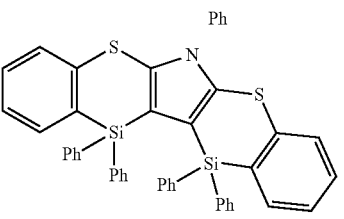
12
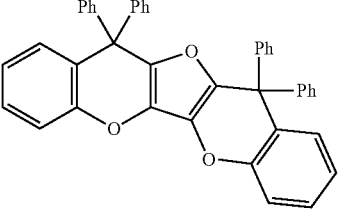

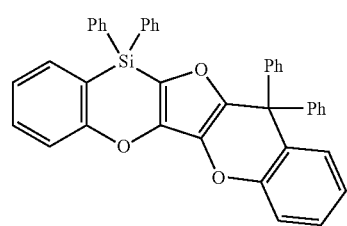
13
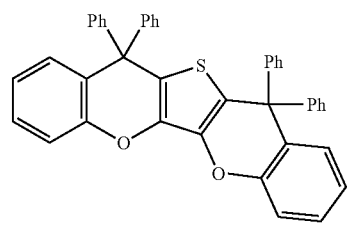
14
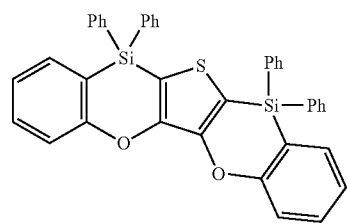
15
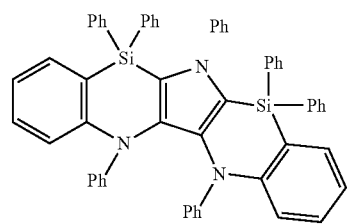
17
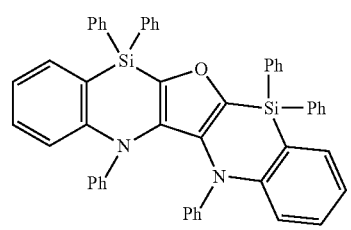
19
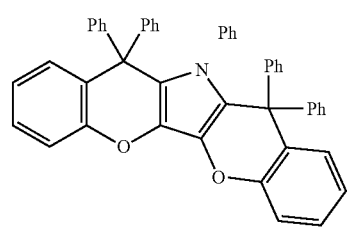
20
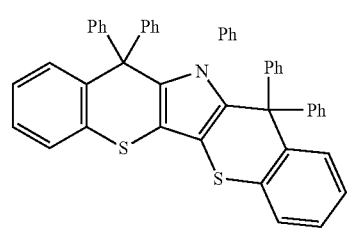
21
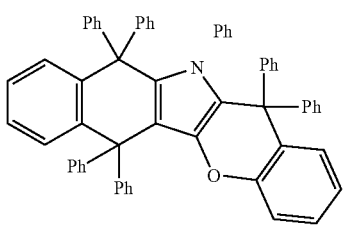
22
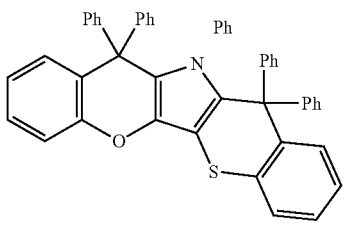
23
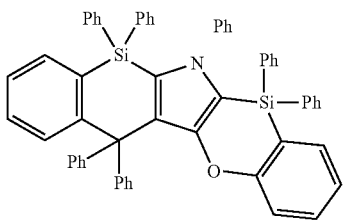
24
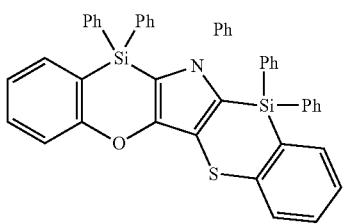
25
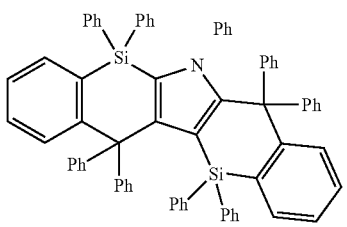
26
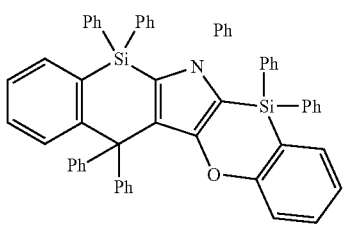
27
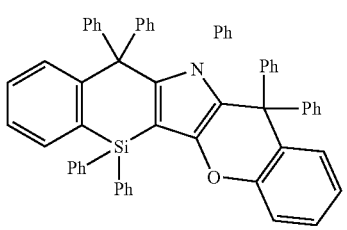
28

29
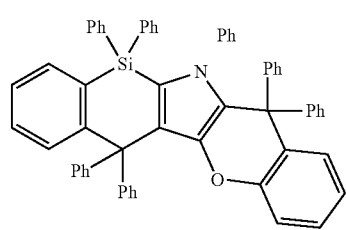
30
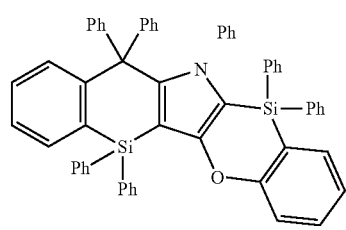
31
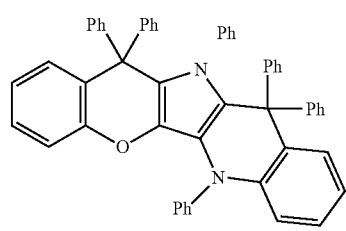
32
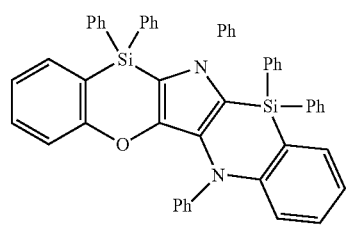
[Compound Group 2]
33
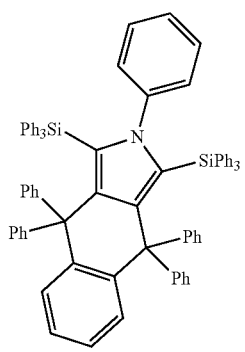
34
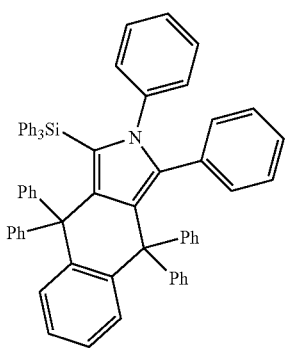
35
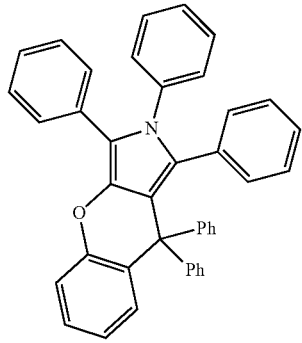
36
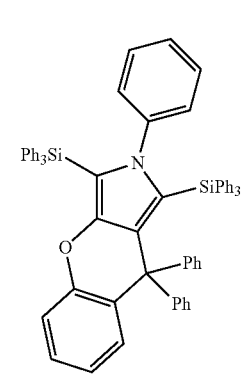
37
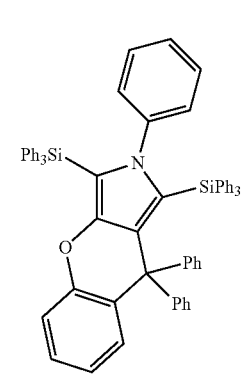
38
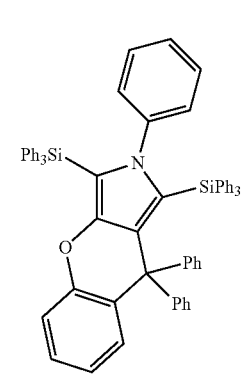

39
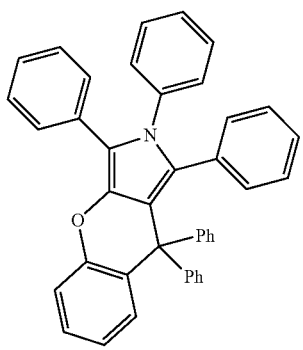
40
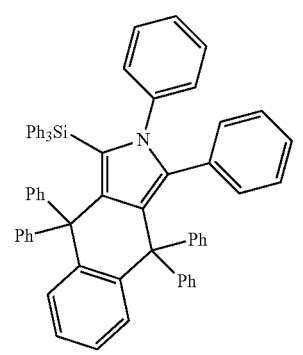
41
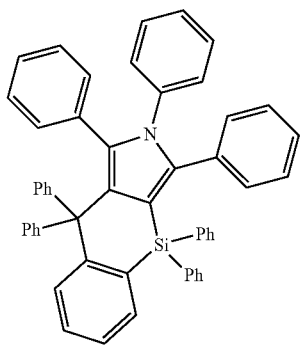
42
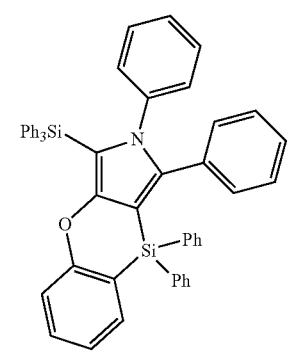
43
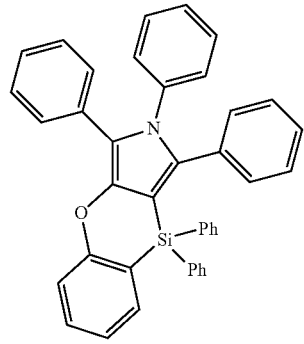
44
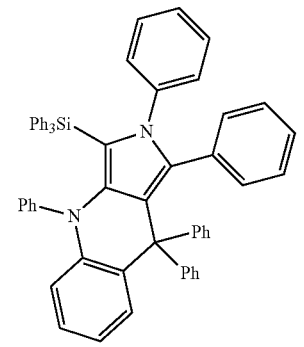
45
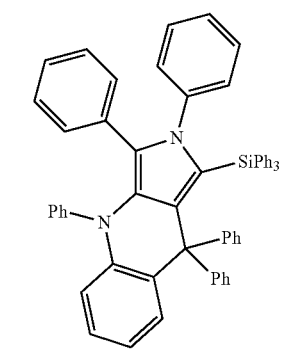
46
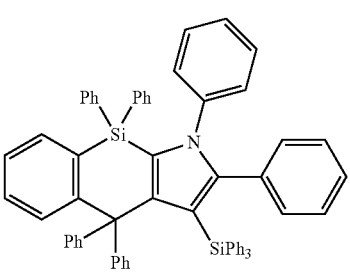
47
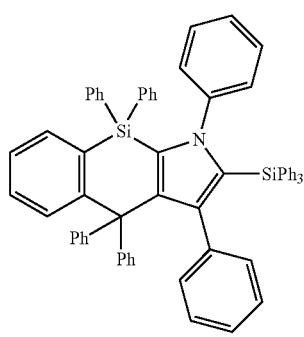

-continued
48
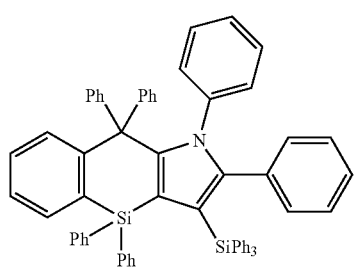
49
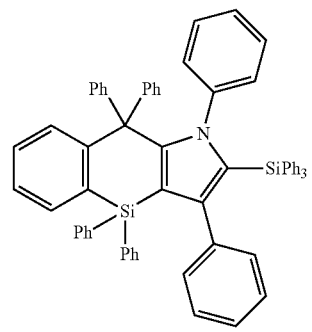
50
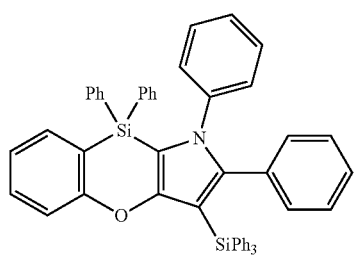
51
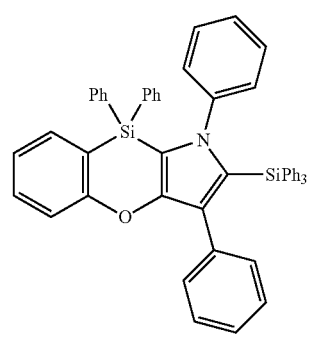
52
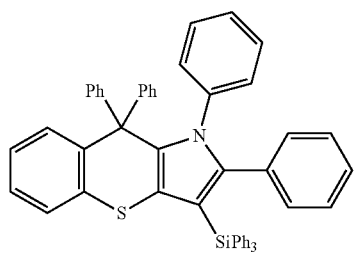
-continued
53
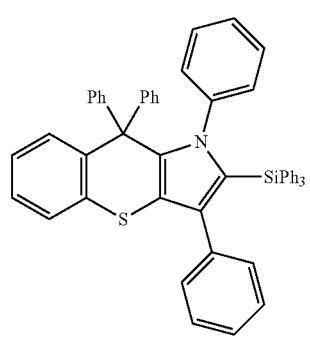
54
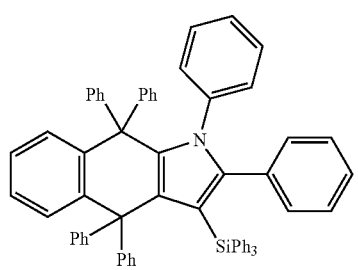
55
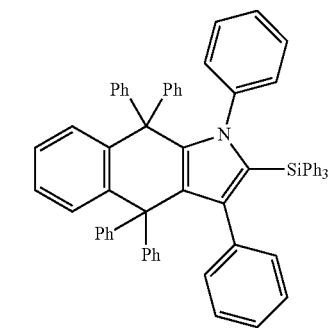
56
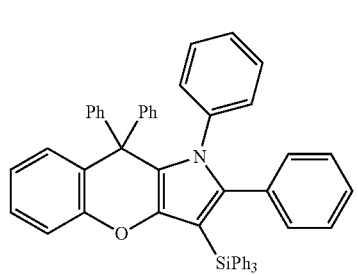
57
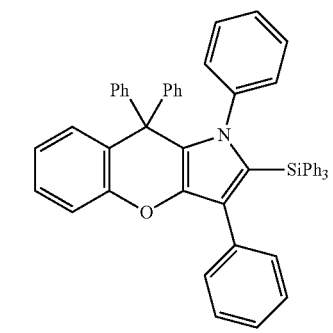

-continued
58 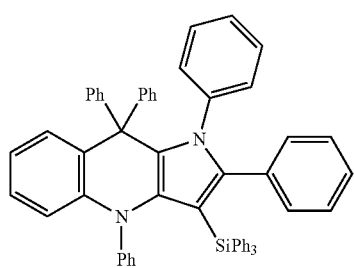
59 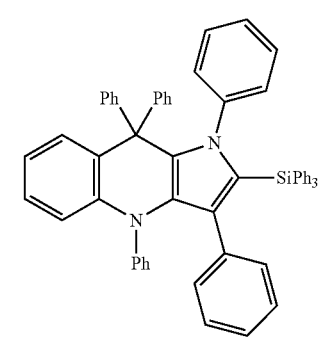
[Compound Group 3]
60 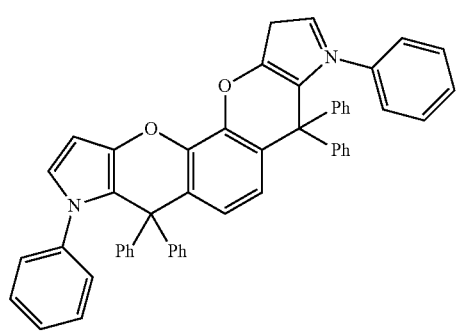
61 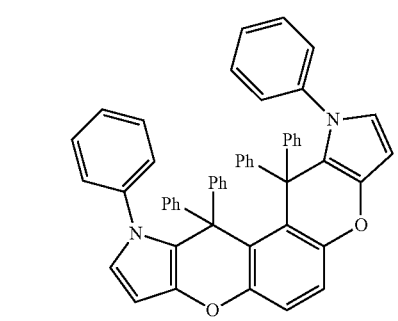
-continued
62 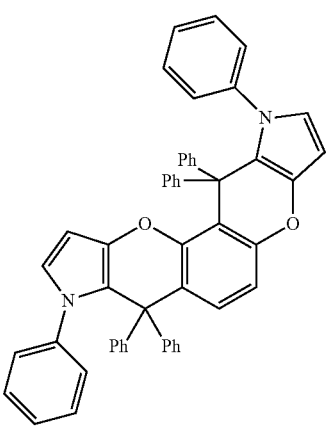
63 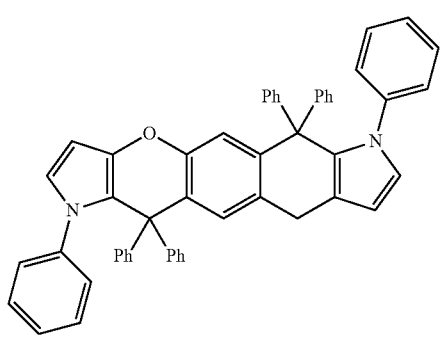
64 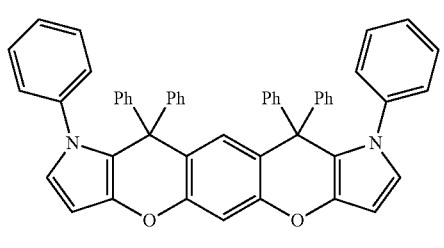
65 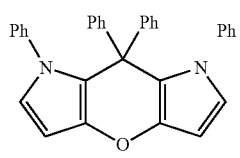
66 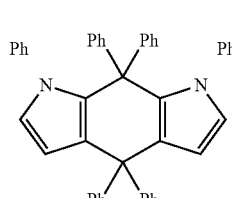
67 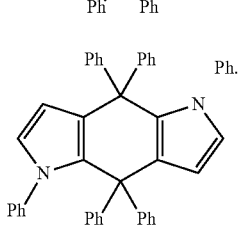
20. A polycyclic compound represented by the following Formula 3-1:

[Formula 3-1]

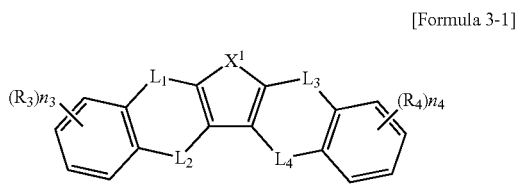

where $X_1$ is one of O, S, or $NY_1$, $R_3$ and $R_4$ are each independently a deuterium atom, a halogen atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted oxy group, a substituted or unsubstituted thio group, a substituted or unsubstituted boron group, a substituted or unsubstituted sulfoxy group, a substituted or unsubstituted phosphine oxide group, a substituted or unsubstituted carbonyl group, a substituted or unsubstituted amino group, or a substituted or unsubstituted silyl group, $n_3$ to $n_4$ are each independently an integer of 0 to 4, and $L_1$ to $L_4$ are each independently a substituted or unsubstituted divalent alkyl group having 1 to 10 carbon atoms, a substituted or unsubstituted divalent silyl group, a substituted or unsubstituted divalent oxy group, or a substituted or unsubstituted divalent thio group, $Y_1$ is a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted boron group, a substituted or unsubstituted sulfoxy group, a substituted or unsubstituted phosphine oxide group, a substituted or unsubstituted carbonyl group, or a substituted or unsubstituted silyl group, wherein when $n_3$ and $n_4$ are each 1, one of $L_1$ and $L_2$ is a divalent thio group, one of $L_3$ and $L_4$ is a divalent thio group, and X1 is S, another one of $L_1$ and $L_2$ and/or another one of $L_3$ and $L_4$ is a divalent alkyl group having 1 to 10 carbon atoms and substituted with a substituted or unsubstituted aryl group having 6 to 15 carbon atoms for forming a ring, or a divalent silyl group substituted with a substituted or unsubstituted aryl group having 6 to 15 carbon atoms for forming a ring.

21. A display device comprising an organic electroluminescence device, wherein the organic electroluminescence device comprises:

a first electrode;

a hole transport region provided on the first electrode;

an emission layer provided on the hole transport region;

an electron transport region provided on the emission layer; and a second electrode provided on the electron transport region, wherein the hole transport region comprises a polycyclic compound represented by the following Formula 1:

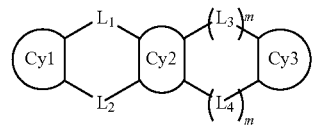

where $L_1$ to $L_4$ are each independently a substituted or unsubstituted divalent alkyl group having 1 to 10 carbon atoms, a substituted or unsubstituted divalent amino group, a substituted or unsubstituted divalent oxy group, a substituted or unsubstituted divalent thio group, a substituted or unsubstituted divalent sulfoxy group, a substituted or unsubstituted divalent phosphine oxide group, or a substituted or unsubstituted divalent silyl group, m is 0 or 1, and Cy1 to Cy3 are each independently represented by the following Formula 2-1 or 2-2, where one of Cy1 or Cy2 is represented by the following Formula 2-2:

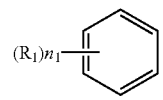

[Formula 2-1]

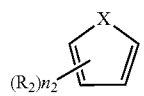

[Formula 2-2]

where X is one of O, S, or $NY_1$, $R_1$ and $R_2$ are each independently a deuterium atom, a halogen atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted oxy group, a substituted or unsubstituted thio group, a substituted or unsubstituted boron group, a substituted or unsubstituted sulfoxy group, a substituted or unsubstituted phosphine oxide group, a substituted or unsubstituted carbonyl group, or a substituted or unsubstituted silyl group, $Y_1$ is a hydrogen atom, a deuterium atom, a halogen atom, a substituted or unsubstituted alkyl group having 1 to 10 carbon atoms, a substituted or unsubstituted aryl group having 6 to 30 carbon atoms for forming a ring, a substituted or unsubstituted heteroaryl group having 2 to 30 carbon atoms for forming a ring, a substituted or unsubstituted boron group, a substituted or unsubstituted sulfoxy group, a substituted or unsubstituted phosphine oxide group, a substituted or unsubstituted carbonyl group, or a substituted or unsubstituted silyl group, $n_1$ is an integer of 0 to 4, and $n_2$ is an integer of 0 to 2, wherein when m is 1, $n_2$ is 0, one of $L_1$ and $L_2$ is a substituted divalent amino group, one of $L_3$ and $L_4$ is a substituted divalent amino group, Cy2 is represented by Formula 2-2, and Cy1 and Cy3 are each represented by Formula 2-1, an other one of $L_1$ and $L_2$ and/or an other one of $L_3$ and $L_4$ is a substituted or unsubstituted divalent amino group, a substituted or unsubstituted divalent oxy group, a substituted or unsubstituted divalent thio group, a substituted or unsubstituted divalent sulfoxy group, a substituted or unsubstituted divalent phosphine oxide group, or a substituted or unsubstituted divalent silyl group, and wherein when m is 0,
i) at least one selected from $L_1$ and $L_2$ is a divalent methyl group substituted with an unsubstituted phenyl group, or a divalent silyl group substituted with a phenyl group, and
ii) when one of $L_1$ and $L_2$ is the divalent methyl group, and when an other one of $L_1$ and $L_2$ is $NY_1$,
  $Y_1$ does not join with an adjacent group to form a ring,
wherein when m is 0 and Cy1 and Cy2 are each represented by Formula 2-2,
  X of Cy1 or Cy2 is O or $NY_1$, and
wherein when m is 1, $n_1$ is 1, one of $L_1$ and $L_2$ is a divalent thio group, one of $L_3$ and $L_4$ is a divalent thio group, Cy2 is represented by Formula 2-2, $n_2$ is 0, X is S, and Cy1 and Cy3 are each represented by Formula 2-1,
an other one of $L_1$ and $L_2$ and/or an other one of $L_3$ and $L_4$ is a divalent alkyl group having 1 to 10 carbon atoms and substituted with a substituted or unsubstituted aryl group having 6 to 15 carbon atoms for forming a ring, a divalent amino group substituted with a substituted or unsubstituted aryl group having 6 to 15 carbon atoms for forming a ring, or a divalent silyl group substituted with a substituted or unsubstituted aryl group having 6 to 15 carbon atoms for forming a ring.

* * * * *